(12) United States Patent
Chen et al.

(10) Patent No.: US 6,258,800 B1
(45) Date of Patent: Jul. 10, 2001

(54) PRODRUGS OF BENZOFURANYLETHYL CARBAMATE NK$_1$ ANTAGONISTS

(75) Inventors: Michael Huai Gu Chen; Om Prakash Goel; Fred M. Hershenson, all of Ann Arbor; Zhijian Zhu, Farmington Hills; Oilun Helen Chan, Canton, all of MI (US)

(73) Assignee: Warner-Lambert Company, Morris Plains, NJ (US)

( * ) Notice: Subject to any disclaimer, the term of this patent is extended or adjusted under 35 U.S.C. 154(b) by 39 days.

(21) Appl. No.: 09/601,570
(22) PCT Filed: Mar. 19, 1999
(86) PCT No.: PCT/US99/06041
  § 371 Date: Aug. 3, 2000
  § 102(e) Date: Aug. 3, 2000
(87) PCT Pub. No.: WO99/52903
  PCT Pub. Date: Oct. 21, 1999

Related U.S. Application Data

(60) Provisional application No. 60/081,881, filed on Apr. 15, 1998.

(51) Int. Cl.$^7$ ............... A61K 31/675; A61K 31/5355; A61K 31/496; C07D 413/14; C07D 405/12; C07D 403/14; A61P 25/06; A61P 11/00; A61P 37/08

(52) U.S. Cl. .................. 514/80; 514/228.2; 514/235.2; 514/254.09; 514/414; 544/143; 544/373; 544/62; 548/454

(58) Field of Search .............. 514/235.2, 254.09, 514/414, 228.2; 544/143, 373, 62; 548/454

(56) References Cited

U.S. PATENT DOCUMENTS 4,760,057 * 7/1988 Alexander et al. .................. 514/187
5,594,022 * 1/1997 Horwell et al. ..................... 514/419

FOREIGN PATENT DOCUMENTS

9749393 * 12/1997 (WO).

* cited by examiner

*Primary Examiner*—Deborah C. Lambkin
*Assistant Examiner*—Andrea D'Souza
(74) *Attorney, Agent, or Firm*—Elizabeth M. Anderson; Charles W. Ashbrook

(57) ABSTRACT

(I)

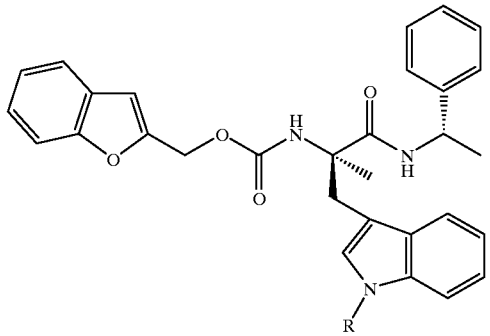

(a)

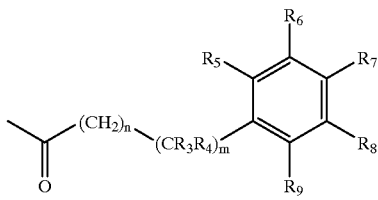

The instant invention provides aqueous soluble prodrugs of formula (I) or a pharmaceutically acceptable salt thereof wherein R is —CH$_2$OZ, —C(=O)OCH$_2$OZ or Z, wherein Z is formula (a), —P(=O)(OH)$_2$ or —C(=O)Q: n is an integer of from 0 to 3; m is an integer of from 0 to 1, of certain tachykinin antagonists (NK$_1$ antagonists) useful in the treatment of emesis.

20 Claims, No Drawings

PRODRUGS OF BENZOFURANYLETHYL CARBAMATE NK₁ ANTAGONISTS

This application is a 371 of PCT/US99/06041 Mar. 19, 1999 which claims benefit of 60/081,881 Apr. 15, 1998.

BACKGROUND OF THE INVENTION

Substance-P, widely distributed throughout the periphery and central nervous system, is believed to mediate a variety of biological actions, via an interaction with three receptor types referred to as $NK_1$, $NK_2$, and $NK_3$, including smooth muscle contraction, pain transmission, neuronal excitation, secretion of saliva, angiogenesis, broncho-constriction, activation of the immune system and neurogenic inflammation.

Accordingly, compounds capable of antagonizing the effects of substance-P at $NK_1$ receptors will be useful in treating or preventing a variety of brain disorders including pain, anxiety, panic, depression, schizophrenia, neuralgia, and addiction disorders; inflammatory diseases such as arthritis, asthma, and psoriasis; gastrointestinal disorders including colitis, Crohn's disease, irritable bowel syndrome, and satiety; allergic responses such as eczema and rhinitis; vascular disorders such as angina and migraine; neuropathological disorders including Parkinson's disease, multiple sclerosis, and Alzheimer's disease; and ophthalmic diseases including scleroderma.

The compounds of the invention provide $NK_1$ receptor antagonists useful as anti-angiogenic agents for the treatment of conditions associated with aberrant neovascularization such as rheumatoid arthritis, atherosclerosis, and tumor cell growth. They will also be useful as agents for imaging $NK_1$ receptors in vivo in conditions such as ulcerative colitis and Crohn's disease.

The compound, 2-benzofuranylmethyl [R-(R*,S*)]-[1-(1H-indol-3-ylmethyl)-1-methyl-2-oxo-2-[(1-phenylethyl)amino]ethyl]carbamate (hereinafter compound 1) is a highly selective $NK_1$ antagonist useful as a pharmacologic agent in the treatment of, for example, emesis. The chemical structure of compound 1 is

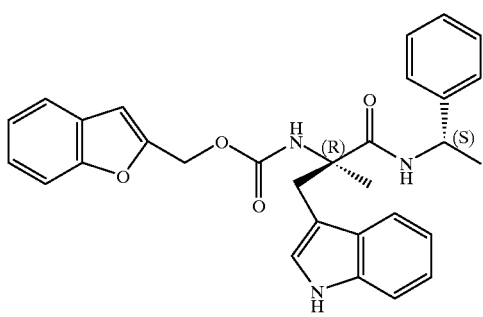

1

Compound 1, processes for its preparation, and methods of using it are claimed in U.S. Pat. No. 5,594,022 hereby incorporated by reference. U.S. patent application Ser. No. 60/021030 claims the use of compound 1 as an antiemetic; it is hereby incorporated by reference.

Compound 1 is poorly soluble in water (less than 1 µg/mL). Therefore, a suitable pharmaceutical formulation, especially an intravenous formulation, is not conveniently achievable using the parent drug substance. The instant invention is a solution to this problem; it is a prodrug of compound 1 with increased aqueous solubility, good solution stability, and high conversion rate to the parent compound in vivo by an enzyme such as an alkaline phosphotase or an esterase. The instant invention utilizes an attachment to the parent molecule, directly or indirectly, of biocleavable, ionizable group(s) such as a phosphate or an amino acid derivative for enhancing aqueous solubility. Due to the lack of readily derivatized functional groups, the only available sites of attachment on compound 1 are the nitrogen of the amide bond; the carbamate bond, and the indole moiety. Although prodrugs derived from amide and carbamate functionalities have been studied in the past, the nitrogen of the indole ring was selected as a more favorable site for prodrug derivatization due to its pKa, chemical reactivity, and relatively less steric encumbrance.

The use of indole nitrogen as the functional group for the preparation of prodrugs is not known in literature. It is the intention of this application to provide a novel prodrug approach by utilizing the indole nitrogen for the preparation of prodrugs. We have now discovered that a hydrophilic and ionizable group, such as a phosphate or an amino acid derivative attached directly or indirectly to an indole nitrogen, can be cleaved enzymatically in vivo. In the indirect attachment approach, a variety of self-cleavable linkers, which were reported to be useful for the hydroxy and amino functional groups in the preparation of prodrugs, were found to be also successful for the indole nitrogen. These linkers include hydroxymethyl (Varia S. A., Schuller S., Sloan K. B., Stella V. J., "Phenytoin prodrugs III: water-soluble prodrugs for oral and/or parenteral use," *J. Pharm. Sci.*,1984;73: 1068–1073; TenHoor C. N., Stewart B. H., "Reconversion of fosphenytoin in the presence of intestinal alkaline phosphatase," *Pharm. Res.*, 1995;12:1806–1809), hydroxymethoxycarbonyl (Safadi M., Oliyai R., Stella V. J., "Phosphoryloxymethyl carbamates and carbonates-novel water-soluble prodrugs for amines and hindered alcohol," *Pharmaceutical Res.*, 1993;10:1350–1355), and masked lactones (Amsberry K. L., Borchardt R. T., "The lactonization of 2'-hydroxyhydrocinnamic acid amides: a potential prodrug for amines," *J. Org. Chem.*, 1990;55:5867–5877; Amsberry K. L., Gerstenberger A. E., Borchardt R. T., "Amine prodrugs which utilize hydroxy amide lactonization. II. A potential esterase-sensitive amide prodrug," *Pharmaceutical Res.*, 1991;8:455–461; Nicolaou M. G., Yuan C-S., Borchardt R. T., "Phosphate prodrugs for amines utilizing a fast intramolecular hydroxy amide lactonization," *J Org. Chem.*, 1996;61 :8636–8641). We have now also discovered that prodrugs of compound 1 derived from both phosphate and amino acid derivatives provide reasonable aqueous solubility and good bio-conversion to the parent compound in vivo.

SUMMARY OF THE INVENTION

The invention covers tachykinin antagonists. The compounds are nonpeptides which have proved to be highly selective and functional tachykinin antagonists. These compounds are unique in the alkylation/substitution pattern along their back bone.

Compounds of the invention are those of Formula I

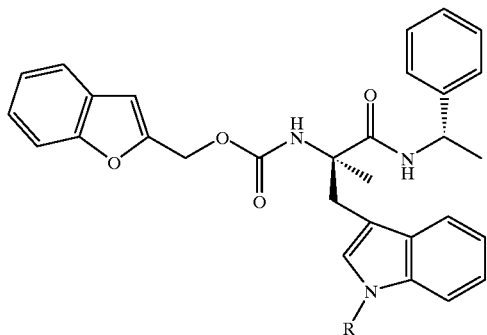

I or a pharmaceutically acceptable salt therof wherein

R is
—CH$_2$OZ;
—C(=O)OCH$_2$OZ or Z;
wherein Z is

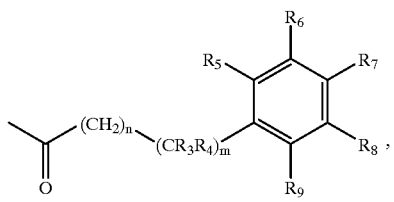

—P(=O)(OH)$_2$, or
—C(=O)Q;

n is an integer of from 0 to 3;

m is an integer of from 0 to 1;

R$_3$ and R$_4$ are each independently hydrogen or alkyl of from 1 to 6 carbons or R$_3$ and R$_4$ are taken together with the carbon to which they are attached to form a cycloalkylidene of from 3 to 6 carbons;

R$_5$–R$_9$ are each independently hydrogen, halogen, alkyl, or alkoxy and one of R$_5$–R$_9$ is —OC(=O)Q, OP(=O)(OH)$_2$, —CH$_2$OC(C=O)Q, —CH$_2$OP(=O)(OH)$_2$, —OH, CH$_2$NR$_1$R$_2$, or NR$_1$R$_2$;

Q is alkyl optionally substituted by —OH, phosphono, phosphooxy, carboxy, or amino, monoalkylamino, or dialkylamino;

R$_1$ and R$_2$ are each independently hydrogen, alkyl optionally substituted with —OH, phosphono, phosphonooxy, carboxy, amino, monoalkylamino, or dialkyl amino or NR$_1$R$_2$ is

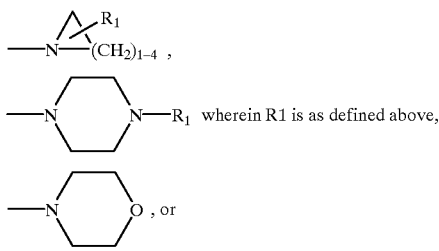

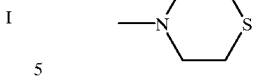

Another aspect of the invention is a pharmaceutical composition comprising an amount of a compound according to Formula I effective to treat respiratory disorders in a mammal suffering therefrom, and a pharmaceutically acceptable carrier.

Another aspect of the invention is a method for treating respiratory disorders in a mammal such as a human comprising administering a therapeutically effective amount of a compound according to Formula I.

Another aspect of the invention is a pharmaceutical composition comprising an amount of a compound according to Formula I effective to treat inflammation in a mammal suffering therefrom, and a pharmaceutically acceptable carrier.

Another aspect of the invention is a method for treating inflammation in a mammal such as a human comprising administering a therapeutically effective amount of a compound according to Formula I.

Another aspect of the invention is a pharmaceutical composition comprising an amount of a compound according to Formula I effective to treat gastrointestinal disorders in a mammal suffering therefrom, and a pharmaceutically acceptable carrier.

Another aspect of the invention is a method for treating gastrointestinal disorders in a mammal such as a human comprising administering a therapeutically effective amount of a compound according to Formula I.

Another aspect of the invention is a pharmaceutical composition comprising an amount of a compound according to Formula I effective to treat eye diseases such as dry eye and conjunctivitis in a mammal suffering therefrom, and a pharmaceutically acceptable carrier.

Another aspect of the invention is a method for treating eye diseases in a mammal such as a human comprising administering a therapeutically effective amount of a compound according to Formula I.

Another aspect of the invention is a pharmaceutical composition comprising an amount of a compound according to Formula I effective to treat allergies in a mammal suffering therefrom, and a pharmaceutically acceptable, carrier.

Another aspect of the invention is a method for treating allergies in a mammal such as a human comprising administering a therapeutically effective amount of a compound according to Formula I.

Another aspect of the invention is a pharmaceutical composition comprising an amount of a compound according to Formula I effective to treat diseases of the central nervous system in a mammal suffering therefrom, and a pharmaceutically acceptable carrier.

Another aspect of the invention is a method for treating diseases of the central nervous system in a mammal such as a human comprising administering a therapeutically effective amount of a compound according to Formula I.

Another aspect of the invention is a pharmaceutical composition comprising an amount of a compound according to Formula I effective to treat migraine in a mammal suffering therefrom, and a pharmaceutically acceptable carrier.

Another aspect of the invention is a method for treating migraine in a mammal such as a human comprising administering a therapeutically effective amount of a compound according to Formula I.

Another aspect of the invention is a pharmaceutical composition comprising an amount of compound according to Formula I effective to treat pain arising from neurogenic inflammation or inflammatory pain.

Another aspect of the invention is a method for treating pain such as pain arising from neurogenic inflammation in inflammatory pain status.

Another aspect of the invention is a pharmaceutical composition comprising an amount of a compound according to Formula I effective in treating conditions associated with aberrant neovascularization: rheumatoid arthritis, atherosclerosis, and tumor cell growth.

Another aspect of the invention is a method of treating conditions associated with aberrant neovascularization: rheumatoid arthritis, atherosclerosis, and tumor cell growth.

Another aspect of the invention is using the compounds as imaging agents for imaging $NK_1$ receptors in vivo.

Processes for preparing the compounds and novel intermediates are included in the invention.

DETAILED DESCRIPTION OF THE INVENTION

The compounds of the instant invention are novel compounds useful in the treatment of various disorders and diseases such as emesis. The compounds are those of Formula I above.

The following terms are descriptive of the compounds.

The alkyl groups contemplated by the invention include straight, branched, or cyclic carbon chains of from 1 to 8 carbon atoms except where specifically stated otherwise. Representative groups are methyl ethyl, propyl, isopropyl, n-propyl, n-butyl, iso-butyl, sec-butyl, 2-methylhexyl, n-pentyl, 1-methylbutyl, 2,2-dimethylbutyl, 2-methylpentyl, 2,2-dimethylpropyl, n-hexyl, and the like.

The cycloalkylidene groups may be cyclopropyl, cyclobutyl, cyclopentyl, cyclohexyl, and cycloheptyl.

The alkoxy groups contemplated by the invention comprise both straight and branched carbon chains of from 1 to 6 carbon atoms unless otherwise stated.

Representative groups are methoxyl, ethoxy, propoxy, i-propoxy, t-butoxy, and hexoxy.

The term halogen is intended to include fluorine, chlorine, bromine, and iodine.

For preparing pharmaceutical compositions from the compounds of this invention, inert, pharmaceutically acceptable carriers can be either solid or liquid.

The compounds of the invention include solvates, hydrates, pharmaceutically acceptable salts, and polymorphs (different crystalline lattice descriptors) of the compounds of Formula I.

The compounds of the present invention can have multiple chiral centers in the above Formula I depending on their structures. In particular, the compounds of the present invention may exist as diastereomers, mixtures of diastereomers, or as the mixed or the individual optical enantiomers. The present invention contemplates all such forms of the compounds.

Where it is appropriate to form a salt, the pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoate (embonate) pantothenate, phosphate/diphosphate, polygalacturonate, salicylate, stearate, subacetate, succinate, sulfate, tannate, tartrate, theoclate, triethiodide, benzathine, chloroprocaine, choline, diethanolamine, ethylenediamine, meglumine, procaine, aluminum, calcium, lithium, magnesium, potassium, sodium, and zinc. Preferred salts are disodium and monohydrochloride.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Biological Data

Male Wistar rats weighing 244 to 390 g were used in the in vivo experiments. The day before the experiment, the rats were surgically prepared. Rats were anesthetized with ether, and the right jugular vein was cannulated for intravenous dosing and/or systemic sampling. The cannula was exteriorized at the nape of the rat between the shoulder blades. The animals were allowed to recover overnight from surgery and fasted with water ad libitum.

Dosing solutions of the prodrugs (5, 25, 18, 34, 20c, 20d, 20e, and 20f) were prepared separately in 5% dextrose in water (D5W). Compound 20a was dissolved in 5% ethanol in D5W whereas compound 29 was dissolved in 20% ethanol, 20% polyethylene glycol 400 in D5W. Animals were randomly assigned to groups of three. The prodrug solutions were administered intravenously as a slow bolus at about 5 mg/kg parent-equivalent or orally as a gastric gavage at about 15 mg/kg parent-equivalent (Table 1 on Page 10 contains PO data). The cannula was subsequently rinsed with 1 mL D5W. Systemic blood was sampled predose and at selected times up to 24 hours after dosing. Blood samples (0.5 mL) were collected on ice, heparinized, and immediately centrifuged; then plasma was harvested and stored at −20° C. until analysis by HPLC.

The plasma samples were analyzed by validated HPLC assay for the parent compound 1. Plasma (200 μL) was spiked with 18 μL of internal standard ([2-(1H-indol-3-yl)-1-methyl-1-(1-phenyl-ethylcarbamoyl)-ethyl]-carbimic acid 4-ethyl-benzyl ester; 2.5 μM) and 400 μL acetonitrile (ACN) to precipitate protein. The supernatant was transferred to a clean test tube and evaporated to dryness. The residue was reconstituted in 50:50 ACN:water and injected onto the HPLC.

Detailed bioconversion data often prodrugs is found in Table 1 below.

TABLE 1

| Compound | Conversion After IV Dosing (%) | Bioavailability After PO Dosing (%) |
|---|---|---|
| 5 | 11.7 ± 0.84 | 9.5 ± 3.9 |
| 25 | 19.9 ± 1.07 | 17.1 ± 4.2 |
| 18 | 59.5 ± 21.3 | 23.0 ± 1.5 |
| 20a | 86.9 ± 18.6 | 16.2 ± 4.9 |
| 29 | 59.4 ± 7.02 | 56.9 ± 18.1 |
| 34 | 9.35 ± 4.12 | |
| 20c | 68.0 ± 5.2 | 36.5 ± 5.5 |
| 20d | 64.2 ± 14.3 | 36.3 ± 8.1 |

TABLE 1-continued

| Compound | Conversion After IV Dosing (%) | Bioavailability After PO Dosing (%) |
|---|---|---|
| 20f | 104.0 ± 38.2 | 46.4 ± 4.2 |
| 20e | 88.5 ± 9.2 | 58.5 ± 20.3 |

Among the first six prodrugs above, the amine (compound 20a) and the amino acid prodrug (29) provide higher conversion than the phosphate prodrugs after intravenous administration, which indicates that the prodrugs are more efficiently cleaved by an esterase than an alkaline phosphatase in vivo in the systemic circulation. Among the phosphate prodrugs, compound 18, with the longest linker, provides the highest reconversion. This indicates that steric-hindrance is one of the factors that limits the bioconversion of these phosphate prodrugs of compound 1 in vivo. Surprisingly; the masked lactone prodrug (34) was found to have the lowest bioconversion in vivo, which is in sharp contrast to the results of literature reports: (A) Amsberry K. L.; Borchardt R. T., "The lactonization of 2'-hydroxyhydrocinnamic acid amides: a potential prodrug for amines,." *J Org. Chem.,* 1990; 55:5867–5877; (B) Amsberry K. L.; Gerstenberger A. E., Borchardt R. T., "Amine prodrugs which utilize hydroxy amide lactonization. II. A potential esterase-sensitive amide prodrug;" *Pharmaceutical Res.,* 1991;8:455–461; of taxol., Oct. 11, 1993; (D) U.S. Pat. No. 5,272,171, Phosphonooxy and carbonate derivatives of taxol., Dec. 21, 1993; (E) Nicolaou M. G.; Yuan C-S., Borchardt R. T., "Phosphate prodrugs for amines utilizing a fast intramolecular hydroxy amide lactonization," *J. Org, Chem.,* 1996;61 :8636–8641.

Since the hydroxymethoxycarbonyI linker in (18) and (20a) appeared to be favorable for rapid reconversion, additional water-soluble prodrugs with the same linker were synthesized and evaluated in the same model. All four newer prodrugs (20c), (20d), (20f), (20e) provided comparable reconversion as (20a) after intravenous administration.

Oral bioavailability of compound 1 was higher after dosing of the amine or amino acid prodrugs compared to the phosphate prodrugs, with the exception of (20a). The success of a prodrug for oral administration depends on several factors: solubility of the prodrug in the gastrointestinal environment, relative stability of the prodrug in intestinal lumen, and rapid reconversion at the brush-border membrane. The phosphate prodrugs were readily soluble, but did not appear to have favorable reconversion in the intestinal tract. (20a) may provide good reconversion, but it was not water-soluble. The four newer prodrugs provide aqueous solubility and favorable reconversion, resulting in reasonable bioavailability of the parent compound.

The following examples are illustrative of the compounds and procedures of the instant invention. They are not intended to limit the scope in any way.

EXPERIMENTAL

The nuclear magnetic resonance (NMR) spectral characteristics refer to chemical shifts (δ) expressed in parts per million (ppm) versus deuterated solvents as reference standard. The nature of the shifts as to multiplicity is reported as broad singlet (bs), singlet (s), multiplet (m), doublet (d), broad doublet (bd), triplet (t), quartet (q). p Some of the abbreviations used herein are listed in the following:

MS: mass spectrometry
Rt: retention time
min: minutes
h: hour
tlc: thin layer chromatography

EXAMPLE 1

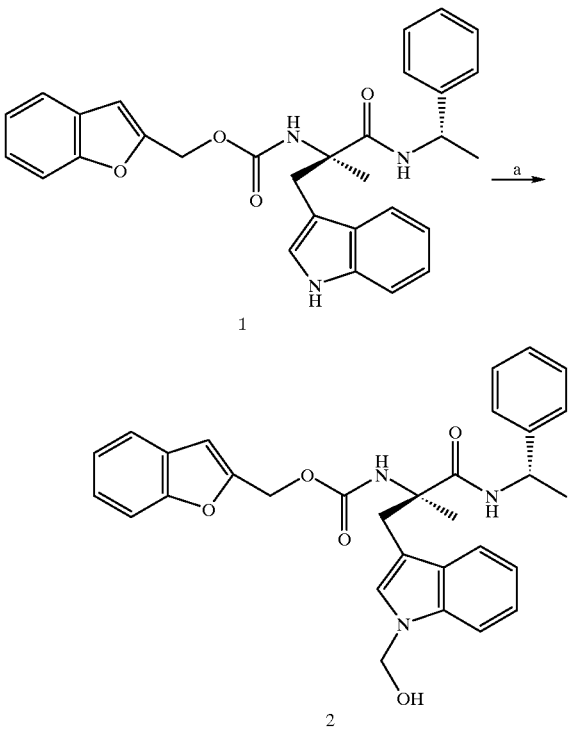

a. 1) KN(TMS)$_2$, THF, -78° C.; 2) CH$_2$O

[2(1-(1-Hydroxymethyl-1H-indol-3-yl)-1-methyl-1-(1-phenylethylcarbamoyl)-ethyl]-carbamic acid benzofuran-2-ylmethyl ester (2)

A solution of KN(TMS)$_2$ in toluene (0.5 M, 10.5 mL, 5.25 mmol) was added dropwise to a solution of compound 1 (2.5 g, 5.05 mmol) in dry THF (70 mL) at -78° C. under N$_2$, and the solution was stirred at -78° C. for 30 minutes. A solution of freshly prepared formaldehyde solution in dry THF (generated by pyrolysis of paraformaldehyde (0.8 g) at 150° C. and bubbled into 30 mL of dry THF) was then added in one portion, and the reaction was stirred at -78° C. for 30 minutes. The reaction mixture was diluted with EtOAc (600 mL) and washed sequentially with saturated NaHCO$_3$ (2×300 mL), saturated NaCl and dried over anhydrous Na$_2$SO$_4$. The solvent was evaporated, and the residue was purified by silica gel chromatography (5.5×6 cm) eluting with CHCl$_3$ to CHCl$_3$/MeOH ( 10:0.1) to give, after evaporation of solvents, compound 2 as a white foam (1.84 g, 70%). An analytical pure sample was obtained by purification through another silica gel column eluted with EtOAc/hexane (1:1) to give a syrup which was dissolved in CH$_3$CN/H$_2$O and lyophilized to give a white solid.

$^1$H NMR (DMSO-d$_6$) δ 8.103 (d, J=8 Hz, 1H), 7.635 (d, J=7.5 Hz, 1H), 7.560 (d, J=8.2 Hz, 1H), 7.51–6.91 (m, 14H), 6.327 (t, J=7 Hz, 1H), 5.355 (m, 2H), 5.201 (q, J=13.3 Hz, 2H), 4.916 (p, J=7.2 Hz, 1H), 3.412 (d, J=14.2 Hz, 1H), 3.251 (d, J=14.2 Hz, 1H), 1.391 (s, 3H), 1.338 (d, J=7 Hz, 3H).

$^{13}$C NMR (DMSO-d$_6$) δ 172.62, 154.44, 154.03, 153.07, 144.68, 135.25, 129.45, 128.06, 127.98, 127.53, 126.40, 126.03, 124.75, 123.00, 121.43, 120.87, 118.92, 118.83, 111.12, 110.08, 109.19, 106.50, 68.42, 59.77, 57.78, 48.14, 23.28, 21.99.

MS (Scan AP+) m/z 507.9 (M−18, 100%).

Anal. Calcd for C$_{31}$H$_{31}$N$_3$O$_5$: C, 70.84; H, 5.94; N, 7.99. Found: C, 70.59; H, 5.88; N, 7.82.

EXAMPLE 2

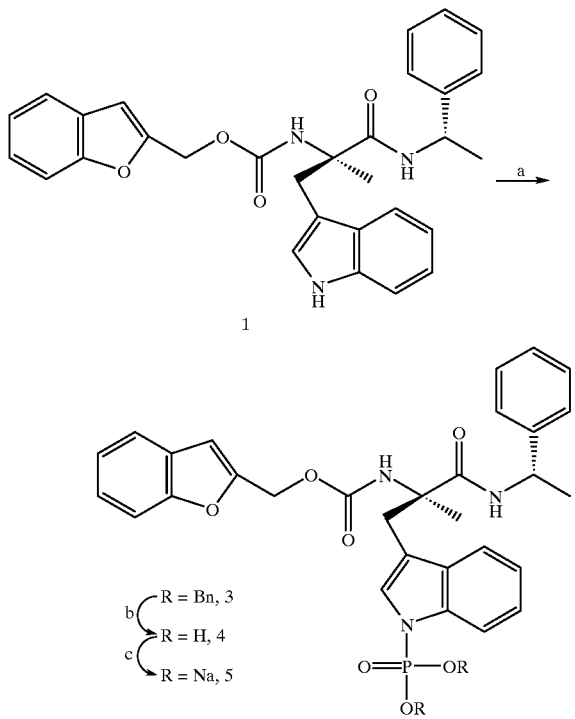

a. 1) KN(TMS)$_2$, THF, −78° C.; 2) ClPO(OBn)$_2$.
b. 1,4-cyclohexadiene, Pd/C, EtOH. c. NaOH, H$_2$O {3-[2-(Benzofuran-2-ylmethoxycarbonylamino)-2-(1-phenyl-ethylcarbamoyl)propyl]-indol-1-yl}-phosphonic acid disodium salt A solution of KN(TMS)$_2$ in toluene (0.5 M, 5.93 mL, 2.97 mmol) was added dropwise to a solution of compound 1 (1.40 g, 2.83 mmol) in dry THF (50 mL) at −78° C. under N$_2$, and the solution was stirred at −78° C. for 30 minutes. A solution of freshly generated dibenzyl phosphoryl chloride (8.5 mmol) in dry THF (5 mL) was then added in one portion, and the reaction was stirred at −78° C. for 30 minutes. The reaction was quenched with a saturated NH$_4$Cl solution (1 mL) and diluted with EtOAc (350 mL). The EtOAc solution was washed sequentially with saturated NaHCO$_3$ (2×100 mL), saturated NaCl and dried over anhydrous Na$_2$SO$_4$. The solvent was evaporated to give a white foam which was purified by silica gel chromatography (5.5×8 cm) by elution with CHCl$_3$ to give compound 3 as a white foam (2.12 g, 99%).

$^1$H NMR (CDCl$_3$) δ 7.642 (d, J=8.3 Hz, 1H), 7.51−7.07 (m, 24H), 6.707 (s, 1H), 6.253 (d, J=7.6 Hz, 1H), 5.342 (bs, 1H), 5.20−4.87 (m, 7H), 3.392 (d, J=15 Hz, 1H), 3.229 (d, J=14.7 Hz, 1H), 1.493 (s, 3H), 1.288 (d, J=6.8 Hz, 3H).

$^{31}$P NMR (CDCl$_3$, external H$_3$PO$_4$/CDCl$_3$) δ −0.285.

MS (Scan AP+) m/z 756.2 (m+1, 7.3%).

Anal. Calcd for C$_{44}$H$_{42}$N$_3$O$_7$P$_1$·¼H$_2$O: C, 69.44; H, 5.59; N, 5.52. Found: C, 69.55; H, 5.75; N, 5.11.

1,4-Cyclohexandiene (1.22 mL, 13 mmol, 10 eq.) was added to a solution of compound 3 (0.978 g, 1.3 mmol) in ethanol (30 mL) in the presence of 10% Pd/C (0.1 g, 10%) under nitrogen and stirred at room temperature for 8 hours. The Pd/C was removed by filtration through celite, and the solid cake was washed with ethanol. The combined filtrate was evaporated under reduced pressure to give a colorless syrup. The product was then purified by silica gel chromatography (4×14 cm) by elution with CH$_3$CN/H$_2$O (9:1) to give after lyophilization, compound 4 as a white solid (0.364 g, 49%, 99.6% purity by HPLC).

$^1$H NMR (CD$_3$OD) δ 7.876 (d, J=8.4 Hz, 1H), 7.518 (d, J=7.8 Hz, 1H), 7.41−7.11 (m, 11H), 7.033 (t, J=7.3 Hz, 1H), 6.870 (t, J=7.3 Hz, 1H), 6.767 (bs, 1H), 5.141 (q, J=13.2 Hz, 2H), 4.933 (q, 1H), 3.398 (d, J=14.1 Hz, 1H), 3.206 (d, J=14.4 Hz, 1H), 1.436 (s, 3H), 1.278 (d, J=6.5 Hz, 3H).

$^{31}$P NMR (CD$_3$OD, external H$_3$PO$_4$/CDCl$_3$) δ −5.449.

MS (Scan ES−) m/z 574.0 (M−1, 100%).

Sodium hydroxide solution (0.1 M) was added to a suspension of compound 4 (100 mg) in water (5 mL) with stirring until pH 8.9, to give a slightly cloudy solution. The solution was then run through a C18 Sep-Pak plug (20 cc, 5 g of C18. Waters), eluted with water to give a clear solution with 100% purity by HPLC. The solution was then lyophilized to give compound 5 as a white solid (95 mg, 86%)

M.P.: >149° C. (turn soft).

$^1$H NMR (CD$_3$OD) δ 8.037 (d, J=8.3 Hz, 1H), 7.52−7.11 (m, 11H), 6.970 (t, J=7.3 Hz, 1H), 6.814 (t, J=7.1 Hz, 1H), 6.746 (bs, 1H), 5.121 (m, 2H), 4.942 (m, 1H), 3.338 (d, J=14.2 Hz, 1H), 3.124 (d, J=14.4 Hz, 1H), 1.451 (s, 3H), 1.241 (d, J=5.1 Hz, 3H).

$^{31}$P NMR (CD$_3$OD, external H$_3$PO$_4$/CDCl$_3$) δ −2.008.

MS (Scan ES+) m/z 620.0 (M+1, 100%).

Anal. Calcd for C$_{30}$H$_{28}$N$_3$O$_7$P$_1$Na$_2$·1.35H$_2$O: C, 55.96; H, 4.81; N, 6.53. Found: C, 55.96; H, 4.64; N, 6.49.

EXAMPLE 3

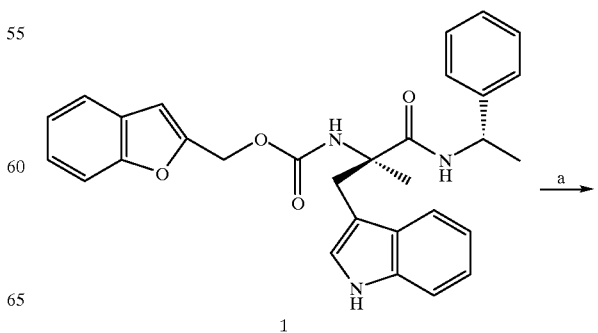

EXAMPLE 4

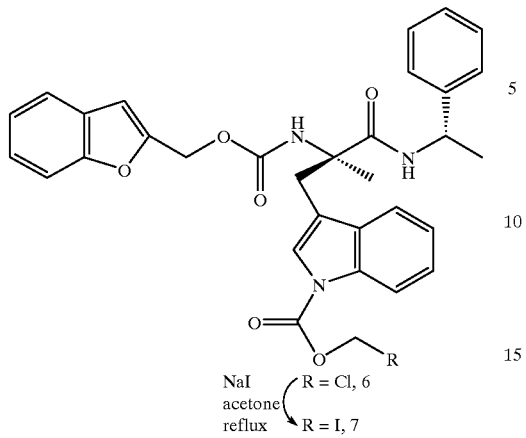

a. 1) KN(TMS)₂, THF, -78° C. 2) chloromethyl chloroformate

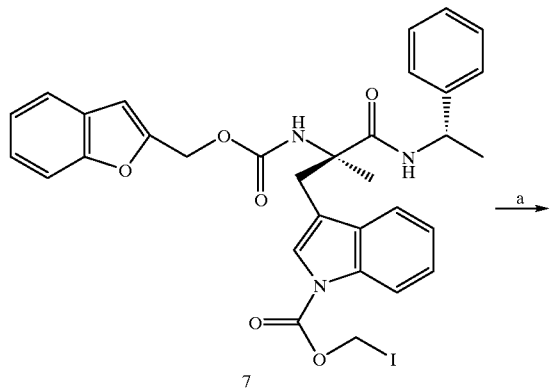

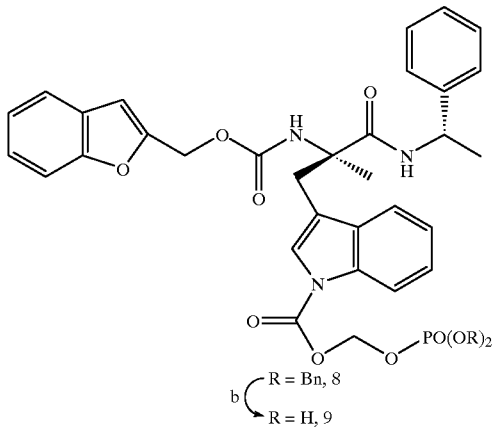

a. AgOPO(OBn)₂, tol, reflux. b. 1,4-cyclohexadiene, 10% Pd/C

3-[2-(Benzofuran-2-ylmethoxycarbonylamino)-2-(1-phenyl-ethylcarbamoyl)propyl]-indol-1-carboxylic acid iodomethyl ester (7)

A solution of KN(TMS)$_2$ in toluene (0.5 M, 0.89 mL, 0.44 mmol) was added dropwise to a solution of compound 1 (0.2 g, 0.4 mmol) in dry THF (10 mL) under N$_2$ at −78° C., and the solution was stirred at −78° C. for 20 minutes. Chloromethyl chloro formate (0.072 mL), 0.81 mmol) was added in one portion and the reaction was stirred at −78° C. for 100 minutes. The solution was then diluted with ethyl acetate (170 mL) and washed with saturated NH$_4$Cl (50 mL), saturated NaHCO$_3$ (2×50 mL) followed by saturated NaCl and dried over anhydrous Na$_2$SO$_4$. The product was purified by silica gel chromatography (3×12 cm) eluting with chloroform to give, after evaporation of the solvent, compound 6 as a white solid (0.235 g, 99%).

$^1$H NMR (CDCl$_3$) δ 8.193 (bs, 1H), 7.53–7.15 (m, 13H), 6.716 (s, 1H), 6.350 (d, J=7.6 Hz, 1H), 5.827 (bs, 2H), 5.431 (bs, 1H), 5.166 (m, 2H), 5.001 (p, J=7 Hz), 3.422 (d, J=14.9 Hz, 1H), 3.311 (d, J=14.9 Hz, 1H), 1.554 (s, 3H), 1.323 (d, J=7.1 Hz, 3H).

$^{31}$C NMR (CDCl$_3$, 172.08, 155.17, 154.58, 152.06, 142.75, 131.32, 128.60, 127.84, 127.30, 126.01, 125.27, 124.85, 123.88, 122.96, 121.34, 119.43, 117.19, 115.28, 111.36, 106.85, 77.31, 77.19, 76.99, 76.67, 70.71, 60.35, 59.08, 49.20, 31.53, 23.98, 21.37.

MS (Scan AP+) m/z 588.1 (M+, 53.5%).

Anal. Calcd for C$_{32}$H$_{30}$N$_3$O$_6$Cl$_1$: C, 64.86; H, 5.15; N, 7.09. Found: C, 64.88; H, 5.24; N, 7.02.

A mixture of compound 6 (2.6 g, 4.42 mmol) and sodium iodide (2.65 g, 17.69 mmol) in acetone (31 mL) was refluxed for 2 hours under N$_2$ to give a yellow suspension. The reaction was diluted with ethyl acetate (200 mL) and washed with water (2×100 mL), saturated Na$_2$S$_2$O$_3$, saturated NaCl, respectively, and dried over anhydrous Na$_2$SO$_4$. The solvent was evaporated under reduced pressure to give compound 7 as a slightly yellow solid (2.92 g, 97.1%).

$^1$H NMR (CDCl$_3$) δ 8.136 (bs, 1H), 7.533–7.153 (m, 13H), 6.719 (s, 1H), 6.345 (d, J=7.3 Hz, 1H), 6.034 (s, 2H), 5.421 (s, 1H), 5.166 (t, 2H), 5.000 (p, J=7 Hz), 3.415 (d, J=14.9 Hz, 1H), 3.304 (d, J=14.6 Hz, 1H), 1.551 (s, 3H), 1.327 (d, J=6.8 Hz, 3H).

The product was used directly in the next step without further purification.

3-[2-(Benzofuran-2-ylmethoxycarbonylamino)-2-(1-phenyl-ethylcarbamoyl)propyl]-indol-1-carboxylic acid phosphooxymethyl ester (9)

Compound 7 (1.21 g, 2.06 mmol), the silver salt of dibenzylphophonate (3.18 g, 8.26 mmol) in dry toluene (60 mL), were refluxed under N$_2$ for 6 hours to give a brown suspension. The solid was removed by filtration through celite, and the solid cake was washed with toluene (50 mL). The combined filtrate was evaporated under reduced pressure to give an oil which was purified by silica gel chromatography (5×8 cm) eluting with CHCl$_3$ to give, after evaporation of solvent, compound 8 as a white foam (1.16 g, 68%).

$^1$H NMR (CDCl$_3$) δ 8.13 (bs, 1H), 7.51–7.13 (m, 23H), 6.702 (s, 1H), 6.286 (d, J=7.9 Hz, 1H), 5.775 (bd, J=13.7 Hz, 2H), 5.287 (bs, 1H), 5.165 (q, J=13.1 Hz, 2H), 5.012 (d, J=8.1 Hz, 4H), 4.981 (m, J=7.4 Hz, 1H), 3.376 (d, J=14.9 Hz, 1H), 3.224 (d, J=14.7 Hz, 1H), 1.496 (s, 3H), 1.296 (d, J=7.1 Hz, 3H).

MS (Scan AP+) m/z 830.2 (M+, 2.3%).

Anal. Calcd for C$_{46}$H$_{45}$N$_3$O$_{10}$P$_1$: C, 66.50; H, 5.46; N, 5.06. Found: C, 66.29; H, 5.54; N, 5.10.

1,4-Cyclohexadiene (2.2 mL, 23.3 mmol) was added to a solution of compound 8 (1.1 g, 1.3 mmol) in ethanol (50 mL) in the presence of 10% Pd/C (0.11 g), and the reaction stirred at room temperature for 6 hours. Additional amount of 1,4-cyclohexadiene (0.5 mL) was added, and the reaction was continuously stirred for an additional 1 hour. The catalyst was removed by filtration through celite, and the solid cake was washed with ethanol. The combined filtrate was evaporated to give a white foam (0.85 g, with 89% purity by HPLC). The product was then purified by silica gel chromatography (4×6 cm) eluting with CH$_3$CN/H$_2$O (9:1) to give, after evaporation of solvents, compound 9 as a white solid (0.36 g, 42%).

$^1$H NMR (CD$_3$OD) δ 8.133 (d, J=8.7 Hz, 1H), 7.969 (d, J=7.8 Hz, 1H), 7.54–6.99 (m, 14H), 6.783 (s, 1H), 5.764 (d, J=13.6 Hz, 2H), 5.205 (m, 2H), 4.936 (p, J=7.1 Hz, 1H), 3.452 (d, J=14 Hz, 1H), 3.227 (d, J=14.7 Hz, 1H), 1.429 (s, 3H), 1.306 (d, J=6.8 Hz, 3H).

$^{31}$P NMR (CD$_3$OD, external H$_3$PO$_4$/CDCl$_3$) δ −0.008.

MS (Scan ES−) m/z 648 (M−H, 7.8%).

EXAMPLE 5

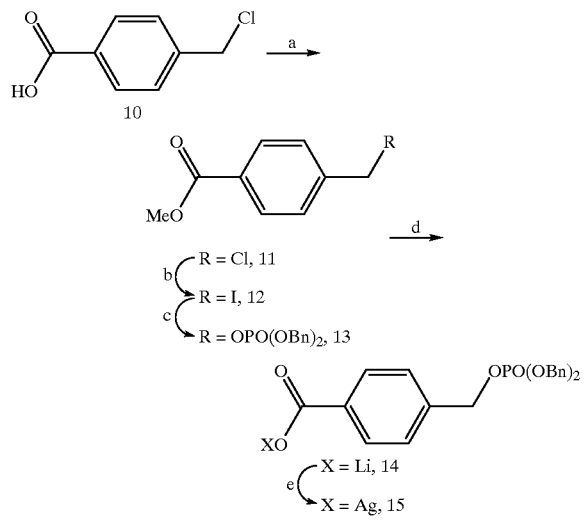

a. CH$_2$N$_2$, Ether, 75%. b. NaI, acetone, reflux, 97%.
c. AgOPO(OBn)$_2$, toluene, reflux, 92%.
d. LiOH, THF, MeOH, H$_2$O. e. AgNO$_3$, H$_2$O, 66% two-steps.

4-(dibenzylphosphoroxymethyl)benzoic acid silver salt (15)

Freshly generated diazomethane was distilled into ether and dropped into a suspension of p-chloromethyl benzoic acid (10, 5 g) in ether (100 mL) at −10° C. until a homogeneous solution was generated. The ether solution was washed with saturated NaHCO$_3$ solution (2×100 mL), saturated NaCl and dried over anhydrous Na$_2$SO$_4$. The ether solution was filtered, and the filtrate was evaporated under reduced pressure to give a colorless oil, which upon standing at room temperature overnight gave methyl p-chloromethyl benzoate (11) as a white solid (4.0 g, 75%).

$^1$H NMR (CDCl$_3$) δ 7.993 (d, 2H), 7.422 (d, 2H), 4.574 (s, 2H), 3.858 (s, 3H).

$^{13}$C NMR (CDCl$_3$) δ 166.52, 142.19, 130.11, 129.98, 128.42, 52.15, 45.32.

A solution of methyl p-chloromethyl benzoate (3.474 g, 18.98 mmol) and NaI (11.39 g, 75.93 mmol) in acetone (80 mL) was refluxed for 2.5 hours to give a yellow suspension. The suspension was concentrated to about 20 mL and diluted with ethyl acetate (400 mL) which was washed with water (2×200 mL), saturated Na$_2$S$_2$O$_3$ (100 mL), saturated NaCl, respectively, and dried over anhydrous Na$_2$SO$_4$. The solvent was evaporated under reduced pressure to give the methyl p-iodomethylbenzoate (12) as a white solid (5.05 g, 97%).

$^1$H NMR (CDCl$_3$) δ 7.927 (d, J=8.3 Hz, 2H), 7.397 (d, J=8.4 Hz, 2H), 4.423 (s, 2H), 3.872 (s, 3H).

The silver salt of dibenzyl phosphate (3.1 g, 8.2 mmol) and compound 12 in dry toluene were refluxed for 4 hours to give a white suspension. The solid was removed by filtration, and the solid cake was washed with toluene. The filtrate was evaporated under reduced pressure to give a colorless syrup which was purified by silica gel chromatography (5×10 cm) eluting with hexane/EtOAc (7:3) to give methyl 4-(dibenzylphosphoroxymethyl)benzoate (13) as a colorless oil (2.13 g, 92%).

$^1$H NMR (CDCl$_3$) δ 7.948 (m, 2H), 7.291 (m, 12H), 5.04–4.96 (m, 6H), 3.879 (s, 3H).

MS (Scan AP+) 427.1 m/z (M+1, 100%).

A solution of LiOH (0.104 g, 2.47 mmol) in water (3 mL) was added to a solution of compound 13 (0.954 g, 2.25 mmol) in THF (15 mL) and methanol (2 mL), and the reaction solution was stirred at room temperature for 15 hours. The solvents were evaporated under reduced pressure to give a colorless oil, which on standing at room temperature gave compound 14 as a white solid. The solid was dissolved in water (50 mL) and acetonitrile (7 mL) and extracted with dichloromethane (30 mL). The dichloromethane layer was discarded, and the aqueous layer was diluted with water to about 250 mL. A solution of silver nitrate (0.343 g, 2.02 mmol, 0.9 eq.) in water (8 mL) was added dropwise to the above solution with stirring to give a white suspension. The suspension was stirred continuously for 15 minutes and let stand at room temperature in dark for 2 hours. The solid was collected by filtration, washed with water and dried under vacuum over P$_2$O$_5$ to give the silver salt of 4-(dibenzylphosphoroxymethyl)-benzoate (15) as a white solid (0.768 g, 66%). This silver salt was used directly for the next coupling reaction.

EXAMPLE 6

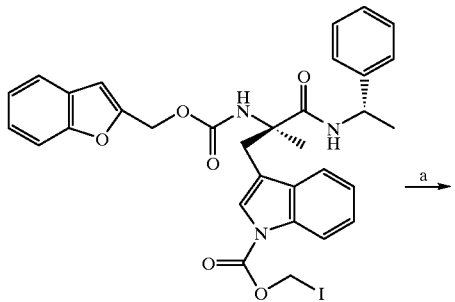

-continued

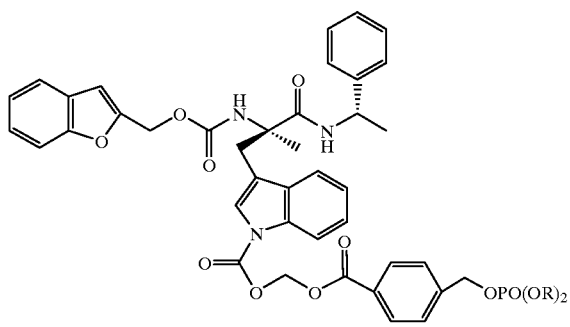

a. AgOOCC$_6$H$_4$CH$_2$OPO(OBn)$_2$, toluene, reflux.
b. 1,4-cyclohexadiene, 10% Pd/C, ethanol.
c. NaOH, H$_2$O.

3-[2-(Benzofuran-2-ylmethoxycarbonylamino)-2-(1-phenyl-ethylcarbamoyl)propyl]-indol-1-carboxylic acid phosphonooxymethylbenzoyloxymethyl ester disodium salt (18)

A suspension of compound (7) (0.332 g, 0.488 mmol) and compound 15 (0.379 g, 0.73 mmol, 1.5 eq.) in toluene (20 mL) was refluxed for 40 minutes to give a brown suspension. The solid was removed by filtration, and the solid cake was washed with toluene. The combined filtrate was evaporated under reduced pressure, and the residue was purified by silica gel chromatography (2.5×8 cm) eluting with chloroform to compound 16 as a white solid (0.354 g, 75%).

$^1$H NMR (CDCl$_3$) δ 8.16 (bs, 1H), 7.948 (d, J=8.3 Hz, 2H), 7.47–7.09 (m, 25H), 6.661 (s, 1H), 6.262 (d, J=7.57 Hz, 1H), 6.151 (bs, 2H), 5.370 (bs, 1H), 5.150 (d, J=13.4 Hz, 1H), 5.088 (d, J=13.2 Hz, 1H), 4.97–4.91 (m, 9H), 3.378 (d, J=14.9 Hz, 1H), 3.249 (d, J=14.9 Hz, 1H), 1.505 (s, 3H), 1.265 (d, J=6.8 Hz, 3H).

MS (AP−) 964.1 m/z (M+1, 9.5%).

Anal. Calcd for C$_{54}$H$_{50}$N$_3$O$_{12}$P$_1$: C, 67.28; H, 5.23; n, 4.36. Found: C, 67.06; H, 5.27; N, 4.28.

Cyclohexa-1,4-diene (0.89 mL, 9.4 mmol, 10 eq.) was added to a solution of compound 16 (0.906 g, 0.94 mmol) in ethanol (25 mL) in the presence of 10% Pd/C (0.09 g) under nitrogen and stirred at room temperature for 5 hours. The catalyst was removed by filtration through celite, and the solid cake was washed with ethanol and ethyl acetate. The filtrate was combined and evaporated under reduced pressure to give compound 17 as a white foam (0.76 g) with 91% purity by HPLC. This was used directly for the generation of the disodium salt. An analytically pure sample of compound 17 was obtained as follows: The crude produce was purified by silica gel chromatography eluting first with CHCl$_3$/MeOH/AcOH (18:1:1) followed by CHCl$_3$/MeOH/AcOH (8:1:1). The pure fractions were combined and evaporated under reduced pressure. The residue was then coevaporated with toluene four times to give a white solid (65%).

$^1$H NMR (DMSO-d$_6$) δ 8.09–6.88 (m, 21H), 6.155 (s, 2H), 5.098 (m, 2H), 4.818 (m, 1H), 4.719 (bs, 2H), 3.335 (d, J=14.4 Hz, 1H), 3.184 (d, J=13.6 Hz, 1H), 1.321 (s, 3H), 1.214 (d, J=6.6 Hz, 3H).

$^{31}$P NMR (DMSO-d$_6$, external H$_3$PO$_4$/CDCl$_3$) δ 0.563.

MS (ES−) 782.3 m/z (M−1, 100%).

Anal. Calcd for C$_{40}$H$_{38}$N$_3$O$_{12}$P$_1$.4/3H$_2$O: C, 59.54; H, 5.02; N, 5.21. Found: C, 59.10; H, 4.70; N, 5.13.

A solution of NaOH (0.0995 M, 18.9 mL) was added slowly to a suspension of crude compound 17 (0.76 g, with 91% purity) in water (20 mL) in an ice bath. After the addition of NaOH, the pH of the slightly cloudy solution was 8.5. The solution was then chromatographed on C18 plug (Waters Sep-Pak Vac 20 cc C18-5 g) eluting first with water and then CH$_3$CH/H$_2$O (1:9) to give, after lyophilization, compound 18 as a white solid (153 mg, 20%) with 99.7% purity by HPLC.

$^1$H NMR (Acetone-d$_6$) δ 8.090 (d, J=7.6 Hz, 1H), 8.035 (d, J=8.3 Hz, 2H), 7.57–7.09 (m, 15H), 6.849 (s, 1H), 6.257 (s, 4H), 5.13 (m, 4H), 4.967 (q, J=7 Hz, 1H), 3.475 (q, J=14.2 Hz, 2H), 1.556 (s, 3H), 1.361 (d, J=7.1 Hz, 3H).

MS (ES−) 781.9 m/z (M+, 74%).

Anal. Calcd for C$_{40}$H$_{36}$N$_3$O$_{12}$P$_1$Na$_2$.3H$_2$O; C, 54.44; H, 4.99; N, 4.76. Found: C, 54.21; H, 4.62; N, 4.69.

EXAMPLE 7

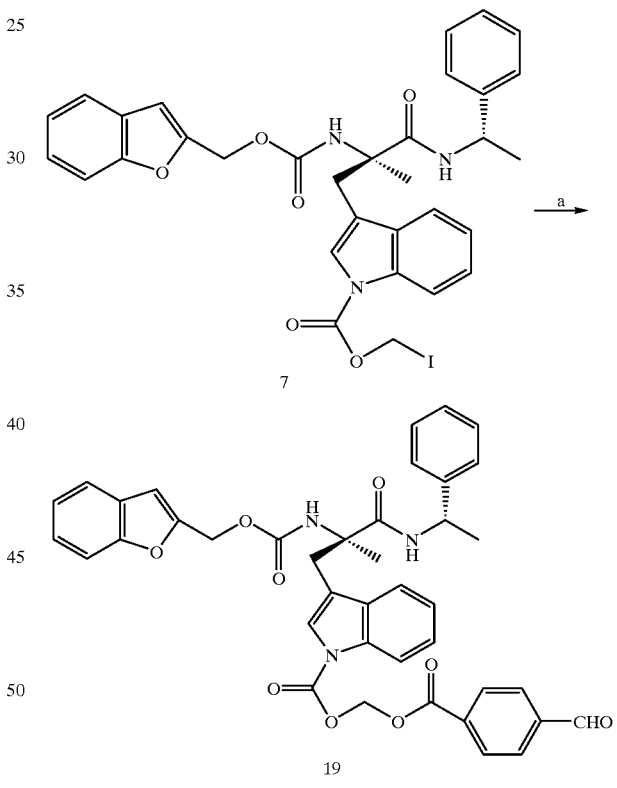

a. p-CHO—C$_6$H$_4$CO$_2$Ag, toluene, reflux.

3-[2-(Benzofuran-2-ylmethoxycarbonylamino)-2-(1-phenyl-ethylcarbamoyl)-propyl]-indole-1-carboxylic acid 4-formylbenzoyloxymethyl ester (19)

A solution of NaOH (0.275 g, 6.87 mmol) in water (3 mL) was added dropwise to a suspension of 4-carboxybenzaldehyde in water (25 mL) to give a clear solution with a small amount of solid. The solid was removed by filtration, and a solution of AgNO$_3$ (1.13 g, 6.66 mmol) in water (3 mL) was added to the filtrate with stirring to give a slightly pale suspension. After stirring at room temperature for 30 minutes, the solid was collected by filtration and dried over $P_2O_5$ under vacuum to give the silver salt of 4-carboxybenzaldehyde as a slightly pale solid (1.47 g, 81%).

Compound 7 (1.7 g, 2.5 mmol) and the silver salt of 4-carboxybenzaldehyde (1.29 g, 5.0 mmol) in dry toluene (50 mL) was refluxed for 30 minutes to give a yellow suspension. The solid was removed by filtration through celite, and the solid cake was washed with toluene. The filtrate was concentrated to give a syrup, which was purified by silica gel column eluting with $CHCl_3$ to give compound 19 as a white foam (1.41 g, 80%).

$^1$H NMR (CDCl$_3$) δ 10.046 (s, 1H), 8.198 (d, J=8.3 Hz, 2H), 8.15 (bs, 1H), 7.897 (d, J=8.3 Hz, 2H), 7.51–7.13 (m, 14H), 6.696 (s, 1H), 6.288 (d, J=7.6 Hz, 1H), 6.206 (bs, 2H), 5.383 (bs, 1H), 5.185 (d, J=13.4 Hz, 1H), 5.112 (d, J=13.2 Hz, 1H), 4.981 (p, 1H), 3.408 (d, J=14.7 Hz, 1H), 3.295 (d, J=14.6 Hz, 1H), 1.547 (s, 3H), 1.311 (d, J=6.9 Hz, 3H).

MS (Scan AP+) 702.3 m/z (M+1, 33.9%).

Anal. Calcd for $C_{40}H_{35}N_3O_9·½H_2O$: C, 67.53; H, 5.07; N, 5.91. Found: C, 67.74; H, 5.44; N, 5.81.

EXAMPLE 8

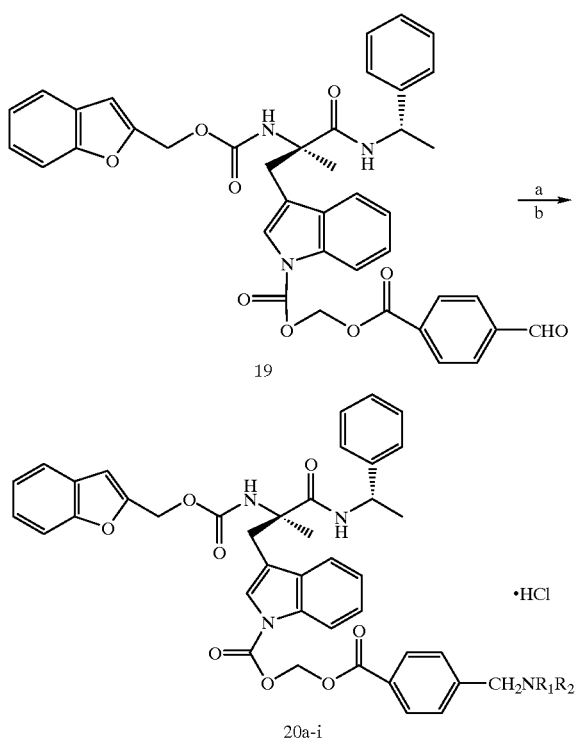

a. HNR$_1$R$_2$, NaHB(OAC)$_3$. b. HCl

3-[2-(Benzofuran-2-ylmethoxycarbonylamino)-2-(1-phenyl-ethylcarbamoyl)-propyl]-indole-1-carboxylic acid 4-dimethylaminomethyl-benzoyloxymethyl ester monohydrochloride salt (20a)

NaBH(AcO)$_3$ (302 mg, 1.41 mmol) was added in three equal portions in 10 minutes to a mixture of compound 19 (0.5 g, 0.713 mmol), dimethylamine hydrochloride (0.116 g, 1.4 mmol), and NaOAc in CHCl$_3$ (10 mL) under nitrogen in an ice bath. The reaction mixture was then stirred in ice bath for 10 minutes and at room temperature for 5 hours. The reaction was then diluted with CHCl$_3$ (100 mL) and washed with saturated NaHCO$_3$ (2×50 mL), saturated NaCl and dried over anhydrous Na$_2$SO$_4$. The product was then purified by silica gel chromatography (3×7 cm) eluting with CHCl$_3$/MeOH (10:0.02 to 10:0.1) to give, after evaporation of solvents, compound 20a as a white foam (0.38 g, 73%).

$^1$H NMR (CDCl$_3$) δ 8.15 (bs, 1H), 8.005 (d, J=8.3 Hz, 2H), 7.52–7.12 (m, 15H), 6.702 (s, 1H), 6.260 (d, J=7.6 Hz, 1H), 6.192 (bs, 2H), 5.397 (bs, 1H), 5.188 (d, J=13.2 Hz, 1H), 5.109 (d, J=13.4 Hz, 1H), 4.971 (p, 1H), 3.417 (m, 4H), 3.271 (d, J=14.6 Hz, 1H), 2.185 (s, 6H), 1.540 (s, 3H), 1.294 (d, J=6.83, 3H).

MS (Scan AP+) 731.4 m/z (M+1, 100%).

$[α]_D^{23}$=+22.66 (C=0.57, MeOH).

Anal. Calcd for $C_{42}H_{42}N_4O_8·¾H_2O$: C, 67.71; H, 5.84; N, 7.52. Found: C, 67.75; H, 5.75; N, 7.42.

A solution of anhydrous HCl in anhydrous ether (0.987 M, 0.2 mL, 0.197 mmol) was added dropwise to a clear solution of compound 20a in ether (20 mL) with stirring. After the addition, the white suspension was stirred at room temperature for 10 minutes, and the solvent was removed under reduced pressure to give a white solid. Ether (2×30 mL) was added to the solid, and the solvent was evaporated to remove excess HCl. The solid was then stirred in water (30 mL) to give a slightly cloudy solution which was lyophilized to the hydrochloride salt of compound 20a as a white powder (127 mg, 97%).

M.P.=turn soft above 110° C.

$^1$H NMR (DMSO-d$_6$) δ 10.629 (bs, 1H), 8.128 (d, J=8.1 Hz, 1H), 8.019 (m, 3H), 7.670 (d, J=7.8 Hz, 2H), 7.586 (d, J=7.6 Hz, 1H), 7.52–7.07 (m, 13H), 6.910 (s, 1H), 6.196 (s, 2H), 5.117 (m, 2H), 4.826 (p, 1H), 4.289 (s, 2H), 3.29 (m, 2H), 2.613 (s, 6H), 1.300 (s, 3H), 1.234 (d, J=6.8 Hz, 3H).

Anal. Calcd for $C_{42}H_{43}N_4O_8Cl·¼H_2O$: C, 65.30; H, 5.64; N, 7.26; Cl, 4.60. Found: C, 65.01; H, 5.89; N, 7.16; Cl, 4.34.

3-[2-(Benzofuran-2-ylmethoxycarbonylamino)-2-(1-phenyl-ethylcarbamoyl)-propyl]-indole-1-carboxylic acid 4-morpholin-4-ylmethyl-benzoyloxymethyl ester monohydrochloride salt (20b)

Morpholine (0.164 mL, 1.88 mmol, 1.1 eq.) and acetic acid (0.108 mL, 1.88 mmol, 1.1 eq.) were added to a solution of compound 19 (1.2 g, 1.71 mmol) in dry dichloromethane (20 mL) under N$_2$ in an ice bath. Then NaHB(OAC)$_3$ (0.508 g, 2.39 mmol, 1.4 eq.) was added in three equal portions in 10 minutes. After the addition, the reaction mixture was stirred for 3 hours at room temperature. A solution of saturated sodium bicarbonate (30 mL) was added to the reaction mixture and stirred at room temperature for 30 minutes. The organic layer was separated and washed sequentially with a solution of saturated sodium bicarbonate (20 mL), a solution of saturated sodium chloride, and dried over anhydrous sodium sulfate. The solvent was evaporated, and the residue was purified by silica gel chromatography eluting with CHCl$_3$/MeOH (10:0.1) to give compound 20b as a white foam (0.921 g, 70%).

$^1$H NMR (CDCl$_3$) δ 8.149 (bs, 1H), 8.003 (d, J=8.05 Hz, 2H), 7.52–7.12 (m, 15H), 6.704 (s, 1H, 6.259 (d, J=7.56 Hz, 1H), 6.914 (bs, 2H), 5.398 (bs, 1H), 5.150 (q, J=13.5 Hz, 2H), 4.972 (p, J=7.1 Hz, 1H), 3.652 (m, 2H), 3.491 (s, 2H), 3.407 (d, J=14.1 Hz, 1H), 3.278 (d, J=14.7 Hz, H), 2.378 (bs, 4H), 1.542 (s, 3H), 1.296 (d, J=6.8 Hz, 3H).

MS (Scan AP+) m/z (M+1, 773.3).

Anal. Calcd for $C_{44}H_{44}N_4O_9·2.2H_2O$: C, 64.99; H, 5.96; N, 6.89. Found: C, 64.61; H, 5.56; N, 6.80.

To a solution of compound 20b (200 mg, 0.26 mmol) in acetonitrile (10 mL) was added a 1.0N HCl solution 0.26 mL, 0.26 mmol, 1 eq.) and stirred at room temperature for 10 minutes. The solvent was evaporated to give a white foam. The white foam was stirred in water (50 mL) to give a white suspension, which was lyophilized to give the hydrochloride salt of compound 20b as a white solid (0.19 g, 91%).

Anal. Calcd for $C_{44}H_{45}N_4O_9Cl.0.5H_2O$: C, 64.52; H, 5.62; N, 6.84. Found: C, 64.61; H, 5.52; N, 6.73.

HPLC: 99.56% purity, Rt=7.04 min (VYDAC, C18, Cat. 218TP54, $CH_3CN$/0.1% TFA in water=50/50, flow rate=1.0 mL/min).

3-[2-(Benzofuran-2-ylmethoxycarbonylamino)-2-(1-phenyl-ethylcarbamoyl)-propyl]-indole-1-carboxylic acid 4-(4-methyl-piperazin-1-methyl)-benzoyloxymethyl ester dihydrochloride salt (20c)

N-methylpiperazine (0.348 mL, 3.14 mmol, 1.1 eq.) and acetic acid (0.359 mL, 6.27 mmol, 2.2 eq.) were added to a solution of compound 19 (2.0 g, 2.85 mmol) in dry dichloromethane (35 mL) under $N_2$ and in an ice bath. NaHB(OAc)$_3$ (0.846 g, 3.99 mmol, 1.4 eq.) was then added in three equal portions over 10 minutes. The reaction was then stirred at room temperature overnight. The reaction mixture was worked up and purified as above to give compound 20c as a white foam (1.504 g, 67%).

$^1$H NMR (CDCl$_3$) δ 8.14 (bs, 1H), 7.995 (d, J=8.1 Hz, 2H), 7.52–7.12 (m, 16H), 6.702 (s, 1H), 6.263 (d, J=7.6 Hz, 1H), 6.19 (bs, 2H), 5.404 (bs, 1H), 5.081 (q, J=13.7 Hz, 2H), 3.497 (s, 2H), 3.411 (d, J=14.7 Hz, 1H), 3.273 (d, J=14.6 Hz, 1H), 2.40 (bs, 8H), 2.238 (s, 3H), 1.539 (s, 3H), 1.294 (d, J=6.8 Hz, 3H).

MS (Scan AP+) m/z (M+1, 786.3).

HPLC: 99.95% purity, Rt=5.26 min (VYDAC, C18, Cat. 128TP54, $CH_3CN$/0.1% TFA in water=50/50, flow rate=1.0 mL/min).

A solution of HCl (1.0N, 1.084 mL, 1.084 mmol, 2 eq.) was added to a solution of compound 20c (0.426 g, 0.542 mmol) and stirred at room temperature for 10 minutes. The solvent was evaporated to give a white foam. The white foam was stirred in water (30 mL) to give a clear solution, which was lyophilized to give the dihydrochloride salt of compound 20c as a white solid (0.425 g, 72%).

Anal. Calcd for $C_{45}H_{49}N_5O_8Cl_2.\frac{3}{4}H_2O$: C, 61.27; H, 5.84; N, 7.94. Found: C, 61.13; H, 5.80; N, 7.88.

HPLC: 99.72% purity, Rt=5.90 min (VYDAC, C18, Column Cat. 218TP54, $CH_3CN$/0.1% TFA in water=50/50, flow rate=1.0 mL/min).

3-[2-(Benzofuran-2-ylmethoxycarbonylamino)-2-(1-phenyl-ethylcarbamoyl)-propyl]-indole-1-carboxylic acid 4-[4-(2-hydroxy-ethyl)-piperazin-1-ylmethyl]-benzoyloxymethyl ester dihydrochloride salt (20d)

NaHB(OAc)$_3$ (0.423 g, 1.996 mmol, 1.4 eq.) was added in three equal portions in 10 minutes to a cloudy solution of compound 19 (1.0 g, 1.43 mmol), N-hydroxyethylpiperazine (0.192 mL, 1.57 mmol, 1.1 eq.) and acetic acid (0.179 mL, 3.14 mmol, 2.2 eq.) in dry chloroform (20 mL) under $N_2$ in an ice bath. The reaction was stirred in ice bath for 30 minutes and at room temperature overnight to give a white suspension. The reaction was worked up as above to give compound 20d as a white foam (0.804 g, 69%).

$^1$H NMR (CDCl$_3$) δ 8.14 (bs, 1H), 8.00 (d, J=8.3 Hz, 2H), 7.52–7.12 (m, 16H), 6.702 (s, 1H), 6.272 (d, J=7.3 Hz, 1H), 6.190 (bs, 2H), 5.411 (bs, 1H), 5.148 (q, J=13.4 Hz, 2H), 4.973 (p, J=6.8 Hz, 1H), 3.549 (m, 2H), 3.502 (s, 2H), 3.409 (d, J=14.9 Hz, 1H), 3.277 (d, J=14.6 Hz, 1H), 2.69 (bs, 1H), 2.50–2.42 (m, 10H), 1.540 (s, 3H), 1.295 (d, J=7.1 Hz, 3H).

MS (Scan AP+) m/z (M+1, 816.2).

Anal. Calcd for $C_{46}H_{49}N_5O_9.1.6H_2O$: C, 65.35; H, 6.18; N, 8.29. Found: C, 64.96; H, 5.89; N, 8.69.

A solution of HCl (1.0N, 0.368 mL, 0.368 mmol) was added to a solution of compound 20d (0.15 g, 0.18 mmol) in acetonitrile (10 mL). The solution was stirred at room temperature for 10 minutes. The solvent was evaporated to give a white foam. The white foam was dissolved in water (10 mL) and then lyophilized to give the dihydrochloride salt of compound 20d as a white solid (0.465 g, 94%).

Anal. Calcd for $C_{46}H_{51}N_5O_9Cl_2.H_2O$: C, 60.87; H, 5.84; N, 7.72. Found: C, 60.62; H, 5.80; N, 7.59.

HPLC: 99.72% purity, Rt=5.28 min (VYDAC, C18, Cat. 218TP54, $CH_3CN$/0.1% TFA in water=50/50, flow rate=1.0 mL/min).

3-[2-(Benzofuran-2-ylmethoxycarbonylamino)-2-(1-phenyl-ethylcarbamoyl)-propyl]-indole-1-carboxylic acid 4-piperazin-1-ylmethyl-benzoyloxymethyl ester dihydrochloride salt (20e)

NaHB(OAc)$_3$ (42 mg, 0.2 mmol, 1.4 eq.) was added to a solution of compound 19 (0.1 g, 0.14 mmol) and piperazine (0.074 g, 0.85 mmol, 6 eq.) in dry chloroform (5 mL) under $N_2$ in an ice bath and stirred 10 minutes. The reaction mixture stirred at room temperature for 19 hours. The reaction was worked up and purified similar as above to give compound 20e as a white foam (47.3 mg, 43%).

$^1$H NMR (CDCl$_3$) δ 8.12 (bs, 1H), 7.967 (d, J=7.1 Hz, 2H), 7.49–7.09 (m, 16H), 6.672 (s, 1H), 6.231 (d, J=7.3 Hz, 1H), 6.160 (bs, 2H), 5.372 (bs, 1H), 5.117 (q, J=13.1 Hz, 2H), 4.941 (p, J=6.6 Hz, 1H), 3.454 (s, 2H), 3.377 (d, J=14.6 Hz, 1H), 3.243 (d, J=14.7 Hz, 1H), 2.822 (m, 4H), 2.341 (bs, 4H), 2.160 (bs, 1H), 1.508 (s, 3H), 1.264 (d, J=7.2 Hz, 3H).

MS (Scan AP+) m/z (M+1, 772.3).

Anal. Calcd for $C_{44}H_{45}N_5O_8.1.5H_2O$: C, 66.09; H, 6.01; N, 8.76. Found: C, 66.29; H, 5.94; N, 8.48.

A solution of HCl (1.0N, 0.35 mL, 0.35 mmol) was added to a solution of compound 20e (0.135 g, 0.175 mmol) in acetonitrile (10 mL). The solution was stirred at room temperature for 10 minutes. The solvent was evaporated to give a white foam. The white foam was dissolved in water (40 mL) and then lyophilized to give the dihydrochloride salt of compound 20e as a white solid (0.13 g, 88%).

Anal. Calcd for $C_{44}H_{47}N_5O_8Cl.1.5H_2O$: C, 60.56; H, 5.74; N, 8.03. Found: C, 60.37; H, 5.69; N, 7.72.

HPLC: 99.12% purity, Rt=4.79 min (VYDAC, C18, Cat. 218TP54, $CH_3CN$/0.1% TFA in water=50/50, flow rate=1.0 mL/min).

3-[2-(Benzofuran-2-ylmethoxycarbonylamino)-2-(1-phenyl-ethylcarbamoyl)-propyl]-indole-1-carboxylic acid 4-{[(2-dimethylamino-ethyl)-methyl-amino]-methyl}-benzoyloxymethyl ester dihydrochloride salt (20f)

NaHB(OAc)$_3$ (0.21 g, 1.0 mmol, 1.4 eq.) was added in three equal portions in 10 minutes to a cloudy solution of compound 19 (0.5 g, 0.713 mmol), N,N,N'-trimethylethylenediamine (0.316 mL, 1.07 mmol, 1.5 eq.) and acetic acid (0.061 mL, 1.07 mmol, 1.5 eq.) in dry chloroform (20 mL) under $N_2$ in an ice bath. The reaction was stirred in ice bath for 30 minutes and room temperature for 20 hours to give a white suspension. Saturated sodium bicarbonate (20 mL) was added to the reaction mixture and stirred for 30 minutes. The organic layer was washed with saturated sodium bicarbonate (30 mL), saturated sodium chloride and dried over anhydrous sodium sulfate. The product was further purified by silica gel chromatography (2.5×6 cm) eluting with $CHCl_3$/MeOH (10:0.5) to give compound 20f as a white foam (0.47 g, 84%).

$^1$H NMR ($CDCl_3$) δ 8.15 (bs, 1H), 7.933 (d, J=7.8 Hz, 2H), 7.52–7.12 (m, 16H), 6.702 (s, 1H), 6.262 (d, J=7.0 Hz, 1H), 6.189 (bs, 2H), 5.397 (bs, 1H), 5.149 (q, J=13.2 Hz, 2H), 4.971 (p, J=7.0 Hz, 1H), 3.516 (bs, 2H), 3.415 (d, J=14.6 Hz, 1H), 3.268 (d, J=14.6 Hz, H), 2.422 (m, 4H), 2.171 (bs, 9H), 1.538 (s, 3H), 1.293 (d, J=6.4 Hz, 3H).

MS (Scan AP+) m/z (M+1, 788.3).

Anal. Calcd for $C_{45}H_{49}N_5O_8 \cdot 0.5H_2O$: C, 67.67; H, 6.27; N, 8.78. Found: C, 67.41; H, 6.44; N, 8.69.

A solution of HCl (1.0N, 1.13 mL, 1.13 mmol) was added to a solution of compound 20f (0.446 g, 0.567 mmol) in acetonitrile (20 mL). The solution was stirred at room temperature for 10 minutes. The solvent was evaporated to give a white foam. The white foam was dissolved in water (30 mL) and then lyophilized to give the dihydrochloride salt of compound 20f as a white solid (0.465 g, 94%).

Anal. Calcd for $C_{45}H_{51}N_5O_8Cl_2 \cdot 2H_2O$: C, 60.27; H, 6.14; N, 7.81. Found: C, 60.58; H, 5.80; N, 7.80.

HPLC: 99.42% purity, Rt=4.42 min (VYDAC, C18, Cat. 218TP54, $CH_3CN$/0.1% TFA in water=50/50, flow rate=1.0 mL/min).

3-[2-(Benzofuran-2-ylmethoxycarbonylamino)-2-(1-phenyl-ethylcarbamoyl)-propyl]-indole-1-carboxylic acid 4-{[bis-(2-hydroxy-ethyl)-amino]-methyl}-benzoyloxymethyl ester monohydrochloride salt (20g)

NaHB(OAc)$_3$ (0.212 g, 1.0 mmol, 1.4 eq.) was added in three equal portions in 10 minutes to a cloudy solution of compound 19 (0.5 g, 0.713 mmol), bis(2-hydroxyethyl) amine (0.15 g, 1.43 mmol, 2.0 eq.) and acetic acid (0.04 mL, 0.71 mmol, 1.0 eq.) in dry dichloromethane (15 mL) under N$_2$ in an ice bath. The reaction was stirred in ice bath for 30 minutes and room temperature for 40 hours to give a white suspension. The reaction was worked up and purified as above to give compound 20g (0.24 g, 42%) as a white foam.

$^1$H NMR ($CDCl_3$) δ 8.14 (bs, 1H), 8.004 (d, J=8.0 Hz, 2H), 7.52–7.12 (m, 16H), 6.702 (s, 1H), 6.291 (d, J=7.3 Hz, 1H), 6.183 (bs, 2H), 5.148 (bs, 1H), 5.147 (q, J=13.4 Hz, 2H), 4.971 (p, J=7.1 Hz, 1H), 3.705 (s, 2H), 3.566 (t, J=6.4 Hz, 4H), 3.408 (d, J=14.9 Hz, 1H), 3.272 (d, J=14.7 Hz, H), 2.651 (t, J=5.4 Hz, 2H), 2.33 (bs, 2H), 1.53 (s, 3H), 1.294 (d, J=6.8 Hz, 3H).

MS (Scan AP+) m/z (M+1, 791.3).

A solution of HCl (1.0 N, 0.506 mL, 0.506 mmol) was added to a solution of compound 20g (0.2 g, 0.253 mmol) in acetonitrile (10 mL). The solution was stirred at room temperature for 10 minutes. The solvent was evaporated to give a white foam. The white foam was stirred in water (40 mL) to give a white suspension, which was lyophilized to give the hydrochloride salt of compound 20g as a white solid (0.19 g, 91%).

Anal. Calcd for $C_{44}H_{47}N_4O_{10}Cl_1 \cdot H_2O$: C, 62.46; H, 5.80; N, 6.62. Found: C, 62.70; H, 5.76; N, 6.62.

HPLC: 99.93% purity, Rt=5.72 min (VYDAC, C18, Cat 218TP54, $CH_3CN$/0.1% TFA in water=50/50, flow rate=1.0 mL/min).

3-[2-(Benzofuran-2-ylmethoxycarbonylamino)-2-(1-phenyl-ethylcarbamoyl)-propyl]-indole-1-carboxylic acid 4-(3-hydroxy-pyrrolidin-1-ylmethyl)-benzoyloxymethyl ester monohydrochloride salt (20h)

NaHB(OAc)$_3$ (0.085 g, 0.4 mmol, 1.4 eq.) was added in three equal portions in 10 minutes to a cloudy solution of compound 19 (0.2 g, 0.285 mmol), 3-hydroxypyrrolidine hydrochloride (0.07 g, 0.57 mmol, 2.0 eq.) and sodium acetate (0.047 g, 0.57 mmol, 2.0 eq.) in dry chloroform (10 mL) under N$_2$ in an ice bath. The reaction was stirred in ice bath for 20 minutes and at room temperature for 4 hours to give a white suspension. The reaction mixture was worked up and purified as above to give compound 20h (0.113 g, 51%) as a white foam.

$^1$H NMR ($CDCl_3$) δ 8.15 (bs, 1H), 8.001 (d, J=8.1 Hz, 2H), 7.52–7.12 (m, 16H), 6.702 (s, 1H), 6.256 (d, J=7.5 Hz, 1H), 6.193 (bs, 2H), 5.392 (bs, 1H), 5.148 (q, J=13.4 Hz, 2H), 4.971 (p, J=7.1 Hz, 1H), 4.291 (m, 1H), 3.631 (s, 2H), 3.416 (d, J=14.7 Hz, 1H), 3.272 (d, J=14.7 Hz, 1H), 2.789 (m, 1H), 2.599 (d, J=9.7 Hz, 1H), 2.494 (m, 1H), 2.250 (m, 1H), 2.133 (m, 1H), 1.799 (bs, 1H), 1.699 (m, 1H), 1.539 (s, 3H), 1.293 (d, J=6.8 Hz, 3H).

MS (Scan AP+) m/z (M+1, 773.2).

Anal. Calcd for $C_{44}H_{44}N_4O_9 \cdot 1.5H_2O$: C, 66.01; H, 5.88; N, 7.00. Found: C, 66.01; H, 5.52; N, 6.88.

A solution of HCl (1.0 N, 0.118 mL, 0.118 mmol) was added to a solution of compound 20h (91 mg, 0.188 mmol) in acetonitrile (10 mL). The solution was stirred at room temperature for 10 minutes. The solvent was evaporated to give a white foam. The white foam was stirred in water (40 mL) to give a white suspension, which was lyophilized to give the hydrochloride salt of compound 20h as a white solid (78 mg, 82%).

Anal. Calcd for $C_{44}H_{45}N_4O_9Cl_1 \cdot H_2O$: C, 63.82; H, 5.68; N, 6.77. Found: C, 63.91; H, 5.83; N, 6.71.

HPLC: 99.83% purity, Rt=6.19 min (VYDAC, C18, Cat. 218TP54, $CH_3CN$/0.1% TFA in water=50/50, flow rate=1.0 mL/min).

1,4-Piperazinediylbis[methylene-4,1-phenylenecarboxymethylene][R-(R*,S*)]-3-[2-[[(2-benzofuranylmethoxy)carbonyl]amino]-2-methyl-3-oxo-3-[(1-phenylethyl)amino]propyl]-1H-indole-1-carboxylate dihydrochloride salt (20i)

Acetic acid (0.082 mL, 1.43 mmol, 1 eq.) was added to a solution of compound 19 (1.0 g, 1.43 mmol) and piperazine (0.246 g, 2.85 mmol, 2 eq.) in dry dichloromethane (20 mL) to give a cloudy solution. The solution was stirred at room temperature for 20 minutes and then cooled by an ice bath. NaBH(OAc)$_3$ (0.423 g, 1.996 mmol, 1.4 eq.) was added in three equal portion in 10 minutes. The reaction mixture was then stirred in ice bath for 10 minutes and at room temperature overnight. The reaction mixture was worked up as above to give Compound 20i (0.544 g, 52%) as a white foam.

$^1$H NMR ($CDCl_3$) δ 8.14 (bs, 1H), 7.981 (d, J=8.3 Hz, 2H), 7.51–7.11 (m, 16H), 6.695 (s, 2H), 6.266 (d, J=7.6 Hz, 1H), 6.182 (bs, 2H), 5.397 (bs, 1H), 5.138 (q, J=13.1 Hz, 2H), 4.965 (p, J=7.1 Hz, 1H), 3.485 (s, 2H), 3.402 (d, J=14.6 Hz, 1H), 3.269 (d, J=14.9 Hz, 1H), 2.39 (bs, 2H), 1.533 (s, 3H, 1.288 (d, J=7.1 Hz, 3H).

MS (Scan ES+) m/z (M+, 1457.6).

Anal. Calcd for $C_{84}H_{80}N_8O_{16} \cdot 3H_2O$: C, 66.67; H, 5.69; N, 7.41. Found: C, 66.67; H, 5.36; N, 7.28

A solution of HCl (1.0 N, 0.275 mL, 0.275 mmol) was added to a solution of compound 20i (0.2 g, 0.137 mmol) in acetonitrile (10 mL). The solution was stirred at room temperature for 10 minutes. The solvent was evaporated to give a white foam. The white foam was stirred in water (40 mL) to give a white suspension, which was lyophilized to give the hydrochloride salt of compound 20i as a white solid (0.18 g, 86%).

Anal. Calcd for $C_{84}H_{82}N_8O_{16}Cl_1 \cdot 3H_2O$: C, 65.92; H, 5.40; N, 7.32. Found: C, 66.30; H, 5.38; N, 7.30.

EXAMPLE 9

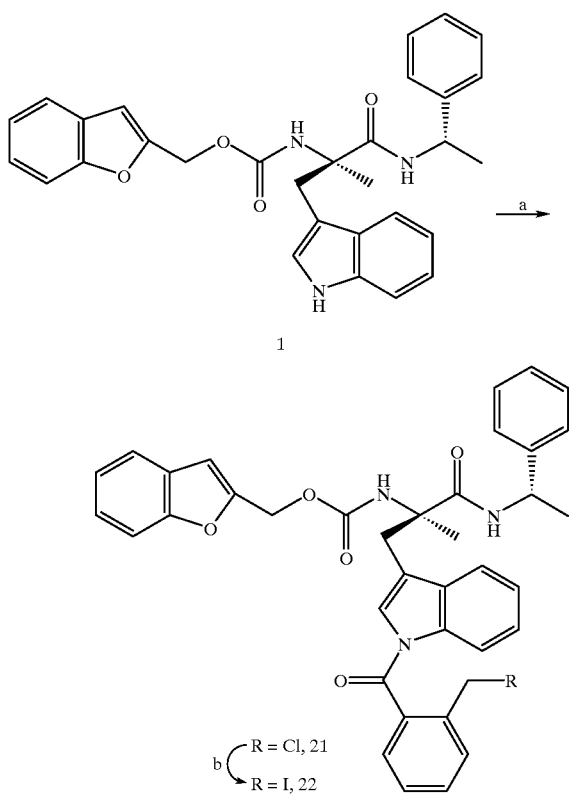

a. 1) KN(TMS)$_2$, THF, -78° C.; 2) 2-(chloromethyl)benzoyl chloride.
b. NaI, acetone, reflux.

{1-Methyl-1-(1-phenyl-ethylcarbamoyl)-2-[1-(2-iodomethylbenzoyl)-1H-indol-3-yl]ethyl}carbamic acid benzofuran-2-ylmethyl ester (22)

A solution of KN(TMS)$_2$ in toluene (0.5 M, 8.88 mL, 4.44 mmol) was added dropwise to a solution of compound 1 (2 g, 4.04 mmol) in dry THF (70 mL) at -78° C. and stirred at -78° C. for 30 minutes. 2-(Chloromethyl)benzoyl chloride (1.14 mL, 8.07 mmol) was then added in one portion, and the reaction solution was continuously stirred at -78° C. for 1 hour. The reaction was diluted with ethyl acetate (600 mL) and washed sequentially with saturated NaHCO$_3$ (3×200 mL), saturated NaCl and dried over anhydrous Na$_2$SO$_4$. The solvent was evaporated, and the residue was purified by silica gel chromatography (5×15 cm) eluting with chloroform to give, after evaporation, compound 21 as a white foam (2.6 g, 99.2%).

$^1$H NMR (CDCl$_3$) δ 8.188 (bd, J=7.6 Hz, 1H), 8.082 (d, J=8 Hz, 1H), 7.64–7.44 (m, 7H), 7.30–7.08 (m, 9H), 6.905 (d, 2H), 6.787 (s, 1H), 5.017 (q, J=13.5 Hz, 2H), 4.747 (m, 3H), 3.265 (q, J=13.5 Hz, 2H), 1.335 (s, 3H), 1.108 (d, J=6.8 Hz, 3H).

MS (Scan AP+) m/z 649.2 (M+).

Anal. Calcd for $C_{38}H_{35}N_3O_5Cl \cdot 1/2H_2O$: C, 69.28; H, 5.47; N, 6.38. Found: C, 69.03; H, 5.11; N, 6.21.

A solution of compound 21 (2.6 g, 4.01 mmol) and NaI (2.49 g, 16.6 mmol) in acetone (50 mL) was refluxed for 2 hours to give a yellow suspension. The suspension was concentrated to about 10 mL and diluted with ethyl acetate (500 mL). The ethyl acetate solution was then washed with water (2×300 mL), saturated Na$_2$S$_2$O$_3$ (100 mL), saturated NaCl and dried anhydrous Na$_2$SO$_4$. The solvent was evaporated to give compound 22 as a slightly yellow foam (2.97 g, quantitative).

$^1$H NMR (CDCl$_3$) δ 8.355 (bd, J=7.8 Hz, 1H), 7.54–7.05 (m, 16H), 6.818 (s, 1H), 6.658 (s, 1H), 6.163 (bd, J=7.3 Hz, 1H), 5.447 (bs, 1H), 5.075 (d, J=13.4 Hz, 1H), 4.988 (d, J=13.2 Hz, 1H), 4.873 (p, J=7.1 Hz, 1H), 4.513 (bs, 2H), 3.297 (q, 2H), 1.532 (s, 3H), 1.180 (d, J=6.8 Hz, 3H).

EXAMPLE 10

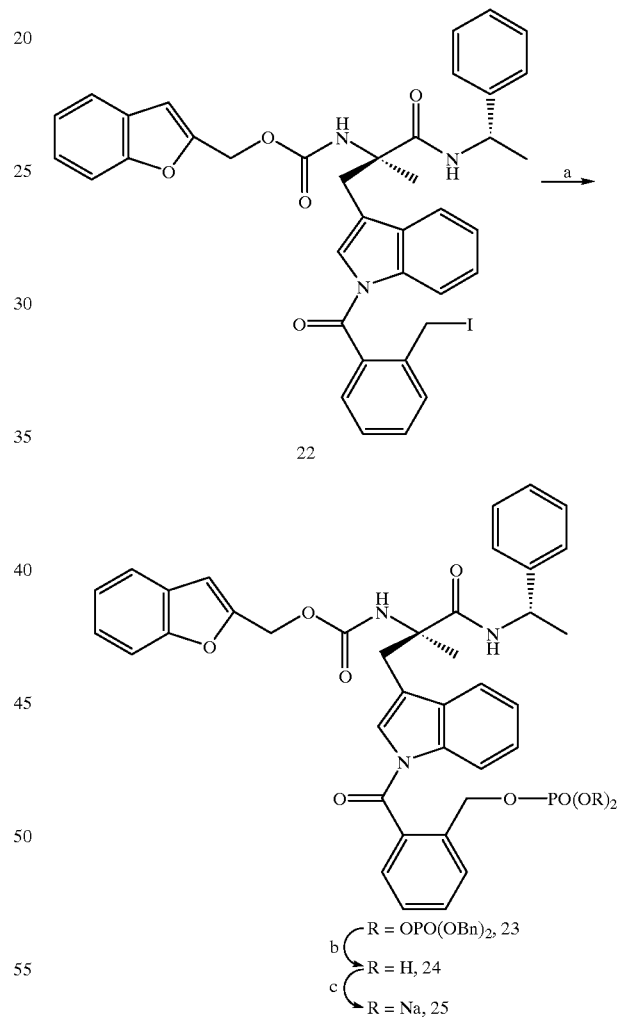

a. AgOPO(OBn)$_2$, toluene, reflux.
b. 1,4-cyclohexadiene, 10% Pd/C, EtOH.
c. 0.1M NaOH, H$_2$O.

{1-Methyl-1-(1-phenyl-ethylcarbamoyl)-2-[1-(2-phosphonooxymethyl-benzoyl)-1H-indol-3-yl]-ethyl}-carbamic acid benzofuran-2-ylmethyl ester disodium salt (25)

A suspension of compound 22 (1 g, 1.35 mmol) and the silver salt of dibenzylphosphate (1.04 g, 2.7 mmol) in toluene was refluxed for 2 hours to give a pale yellow suspension. After cooling to room temperature, the solid was removed by filtration through celite, and the solid cake was washed with toluene. The combined filtrate was evaporated under reduced pressure to give a yellow syrup which was purified by silica gel chromatography (2.5×8 cm) eluting with CHCl$_3$ to give compound 23 as a white foam (1.002 g, 83.4%).

$^1$H NMR (CDCl$_3$) δ 8.654 (bs, 1H), 7.567 (d, J=7.8 Hz, 1H), 7.44–7.03 (m, 25H), 6.646 (s, 1H), 6.558 (bs, 2H), 5.078 (d, J=13.2 Hz, 1H), 5.0–4.8 (bm, 3H), 4.7–4.5 (m, 6H), 3.523 (d, J=14.2 Hz, 1H), 3.189 (d, J=14.6 Hz, 1H), 1.343 (s, 3H), 1.185 (d, J=6.6 Hz, 3H).

MS (Scan AP+) m/z 890.3 (M+1, 41%).

Anal. Calcd for C$_{52}$H$_{48}$N$_3$O$_9$P$_1$: C, 70.18; H, 5.44; N, 4.72. Found: C, 70.32; H, 5.47; N, 4.78.

1,4-Cyclohexandiene (1.38 mL, 14.6 mmol, 13 eq.) was added to a solution of compound 23 (1.0 g, 1.12 mmol) in ethanol in the presence of 10% pD/C (0.1 g) under nitrogen and stirred at room temperature for 9 hours. The catalyst was removed by filtration through celite, and the solid cake was washed with ethanol. The combined filtrate was then concentrated under reduced pressure to give a colorless syrup (0.77 g, with 80% purity by HPLC). The product was then purified by preparative HPLC (C18, VYDAC, 78/250 mm, 10–15μ) eluting with CH$_3$CN/0.1% TFA in water (50/50) to give, after evaporation and lyophilization, compound 24 as a white solid (0.535 g, 67%).

$^1$H NMR (CD$_3$OD) δ 8.307 (d, J=8.2 Hz, 1H), 7.653 (d, J=7.7 Hz, 1H), 7.58–7.14 (m, 17H), 6.826 (bs, 1H), 6.779 (bs, 1H), 5.101 (bs, 2H), 4.92 (m, overlapped partially with CD$_3$O_D_), 3.402 (d, J=14.5 Hz, 1H), 4.8 (overlapped with CD$_3$OD), 1.404 (s, 3H), 1.280 (d, J=7 Hz, 3H).

MS (Scan ES−) m/z 708.5 (M-1, 100%).

Anal. Calcd for C$_{38}$H$_{36}$N$_3$O$_9$P$_1$.1H$_2$O: C, 62.66; H, 5.22; N, 5.77. Found: C, 62.80; H, 5.03; N, 5.78.

Compound 24 (0.462 g, 0.635 mmol) was suspended in water (30 mL) and titrated with sodium hydroxide (0.102 M, 12.47 mL, 2 eq.) to give a clear solution with pH 8.4. The solution was lyophilized to give the disodium 25 as a white solid (0.49 g, quantitative).

M.P.=152–156° C.

$^1$H NMR (CD$_3$OD) δ 8.272 (d, J=8 Hz, 1H), 7.955 (d, J=7.6 Hz, 1H), 7.088–7.545 (m, 17H), 6.808 (s, 1H), 6.749 (s, 1H), 5.00 (m, 3H), 3.395 (d, J=14.4 Hz, 1H) 3.228 (d, J=14.6 Hz, 1H), 1.376 (s, 3H), 1.258 (d, J=6.6 Hz, 3H).

$^{31}$P NMR (CD$_3$OD, external H$_3$PO$_4$/CDCl$_3$) δ 5.599.

MS (Scan ES−) m/z 708.0 (M-1, 39%).

Anal. Calcd for C$_{38}$H$_{34}$N$_3$O$_9$P$_1$Na$_2$.2.5H$_2$O: C, 57.09; H, 4.88; N, 5.26. Found: C, 57.10; H, 4.72; N, 5.21.

EXAMPLE 11

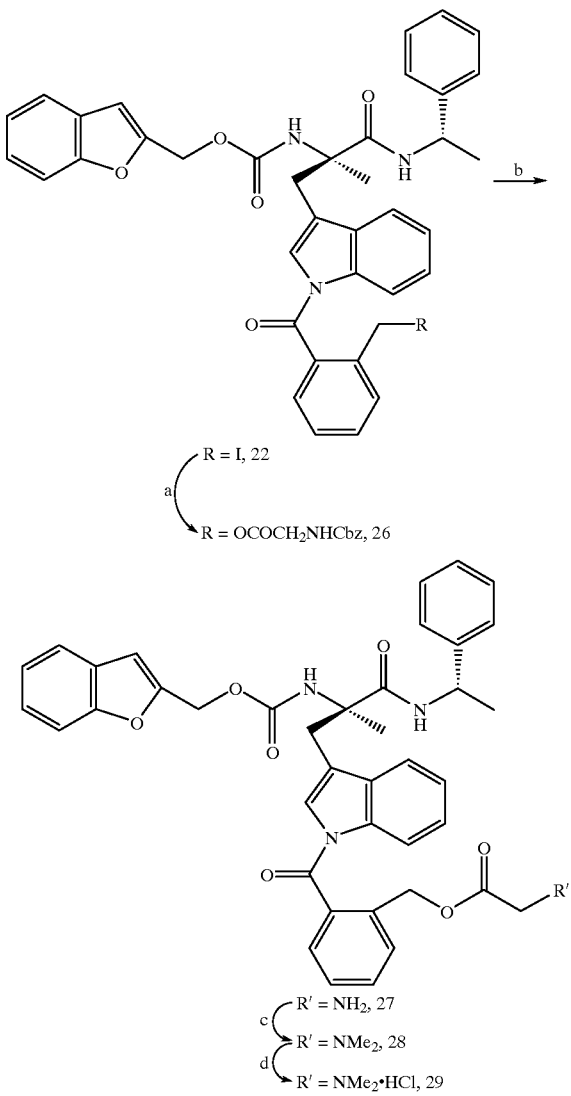

a. AgO$_2$CCH$_2$NHCbz, toluene, reflux, 85%.
b. HCOOH, DMF, r.t., 40%.
c. 37% CH$_2$O, NaOAc, HOAc, NaCNBH$_3$, MeOH, 84%. d. HCl, 97%.

3-[2-(Benzofuran-2-ylmethoxycarbonylamino)-2-(1-phenyl-ethylcarbamoyl)-propyl]-indole-1-carboxylic acid 4-dimethylaminomethyl-benzoyloxymethyl ester monohydrochloride salt (29)

A solution of NaOH (1.808 g, 45.2 mmol) in water (10 mL) was added to a suspension of N-Cbz-glycine (9.46 g, 45.2 mmol) in water (200 mL dropwise at room temperature to give a clear solution. After stirring for 10 minutes, a solution of AgNO$_3$ in water (10 mL) was added dropwise in dark to give a white suspension. After stirring for 30 minutes, the solid was collected by filtration and washed with water (50 mL). The solid was then dried over P$_2$O$_5$ under vacuum to give the silver salt of N-Cbz-glycine (12.77 g, 89.3%).

The silver salt of N-Cbz-glycine (1.5 g, 4.76 mmol) and compound 22 (1.76 g, 2.38 mmol) in dry toluene (50 mL) were refluxed for 30 minutes to give a yellow suspension. The solid was filtered off through celite, and the solid cake was washed with toluene (20 mL). The filtrate was concentrated to give a syrup and purified by silica gel chromatography (5×10 cm) eluting with CHCl₃ to give compound 26 as a white foam (1.66 g, 85%).

¹H NMR (CDCl₃) δ 8.198 (bs, 1H), 7.54–7.10 (m, 21H), 6.801 (s, 1H), 6.601 (s, 1H), 6.502 (bs, 1H), 5.929 (bs, 1H), 5.241 (d, J=12.5 Hz, 1H), 5.166 (d, J=12.5 Hz, 1H), 5.022 (m, 1H), 4.883 (m, 4H), 3.503 (m, 2H), 3.367 (bs, 2H), 1.468 (s, 3H), 1.306 (bs, 1H), 1.139 (d, J=6.8 Hz, 3H).

MS (Scan AP+) m/z 821.3 (M+, 42%).

Formic acid (1.7 mL, 45 mmol) was added to a mixture of compound 26 (0.853 g, 1.0 mmol), 10% Pd/C (0.17 g) in DMF (17 mL) and stirred at room temperature under N₂ for 5 hours. The Pd/C was removed by filtration, and the filtrate was evaporated under reduced pressure to give a syrup. The syrup was then dissolved in EtOAc (100 mL) and washed with saturated NaHCO₃ (2×50 mL), saturated NaCl and dried over anhydrous Na₂SO₄. The solvent was evaporated, and the residue was purified by silica gel chromatography (5×8 cm) eluting with CHCl₃/MeOH (10.02) to give, after evaporation of solvents, compound 27 as a white foam (0.287 g, 40.2%).

¹H NMR (CDCl₃) δ 8.23 (bs, 1H), 7.56–7.10 (m, 16H), 6.776 (bs, 1H), 6.622 (s, 1H), 6.494 (d, J=7.6 Hz, 1H), 6.3 (bs, 1H), 5.240 (d, J=13.2 Hz, 1H), 5.158 (d, J=12.9 Hz, 1H), 5.027 (d, J=13.2 Hz, 1H), 4.924 (p, J=7.1 Hz, 1H), 4.77 (bd, 1H), 3.445 (d, J=14.4 Hz, 1H), 3.257 (d, J=14.6 Hz, 1H), 2.916 (m, 2H), 1.443 (s, 3H), 1.226 (d, J=6.8 Hz, 3H), 1.05 (bs, 2H).

MS (Scan AP+) m/z 687.3 (M+, 100%).

NaCNBH₃ (0.126 g, 2.0 mmol) was added portionwise to a solution of compound 27 (0.251 g, 0.365 mmol), NaOAc (1.37 g, 16.7 mmol), HOAc (1 mL, 18 mmol) and 37% aqueous formaldehyde (2.5 mL, 30.8 mmol) in MeOH (8 mL) at room temperature in 20 minutes. The reaction was then stirred at room temperature for 10 minutes. The reaction solution was then concentrated under reduced pressure and diluted with EtOAc (100 mL). The EtOAc solution was washed with saturated Na₂CO₃ (2×50 mL), saturated NaCl and dried over anhydrous Na₂SO₄. The solvent was evaporated, and the syrup was purified by silica gel chromatography (3×5 cm) eluting with CHCl₃/MeOH (10:0.02) to give compound 28 as a white foam (0.22 g, 84%).

¹H NMR (CDCl₃) δ 8.348 (bs, 1H), 7.54–7.15 (m, 17H), 6.665 (bs, 1H), 6.610 (s, 1H), 6.515 (bs, 1H), 5.38 (bd, 1H), 5.076 (d, J=13.4 Hz, 1H), 5.01 (bd, 1H), 4.916 (p, J=7.1 Hz, 1H), 4.6 (bs, 1H), 3.444 (d, J=14.7 Hz, 1H), 3.253 (d, J=14.7 Hz, 1H), 2.857 (d, J=17.1 Hz, 1H), 2.695 (d, J=17.1 Hz, 1H), 1.987 (s, 6H), 1.356 (s, 3H), 1.211 (d, J=6.8 Hz, 3H).

MS (Scan AP+) m/z 715.3 (M+1, 100%).

Anal. Calcd for C₄₂H₄₃N₄O₇·H₂O: C, 68.69; H, 6.13; N, 7.63. Found: C, 68.88; H, 5.90; N, 7.73.

Hydrogen chloride in diethyl ether (0.987 M, 0.16 mL, 0.16 mmol) was added to a solution of compound 28 (100 mg, 0.14 mmol) in dry ethyl ether (20 mL) at room temperature under N₂ over 10 minutes. The white suspension was stirred for 10 minutes in an ice bath. The solvent was evaporated under reduced pressure. Ether (2×50 mL) was added to the solid, and the solvent was evaporated to remove excess HCl. The solid was then stirred in water (40 mL) to give a cloudy solution which was lyophilized to give compound 29 as a white solid (101 mg, 96.9%).

¹H NMR (DMSO-d₆) δ 10.214 (bs, 1H), 8.264 (d, J=7.6 Hz, 1H), 8.188 (d, J=7.9 Hz, 1H), 7.64–7.09 (m, 16H), 6.910 (s, 2H), 6.773 (s, 1H), 5.243 (q, J=13, 2H), 5.014 (q, J=13.5 Hz, 2H), 4.701 (p, 2H), 3.832 (m, 2H), 3.297 (s, 2H), 2.555 (s, 6H), 1.385 (s, 3H), 1.106 (d, J=6.8 Hz, 3H).

Anal. Calcd for C₄₂H₄₄N₄O₇Cl₁: C, 67.06; H, 5.90; N, 7.45. Found: C, 66.79; H, 5.60; N, 7.30.

EXAMPLE 12

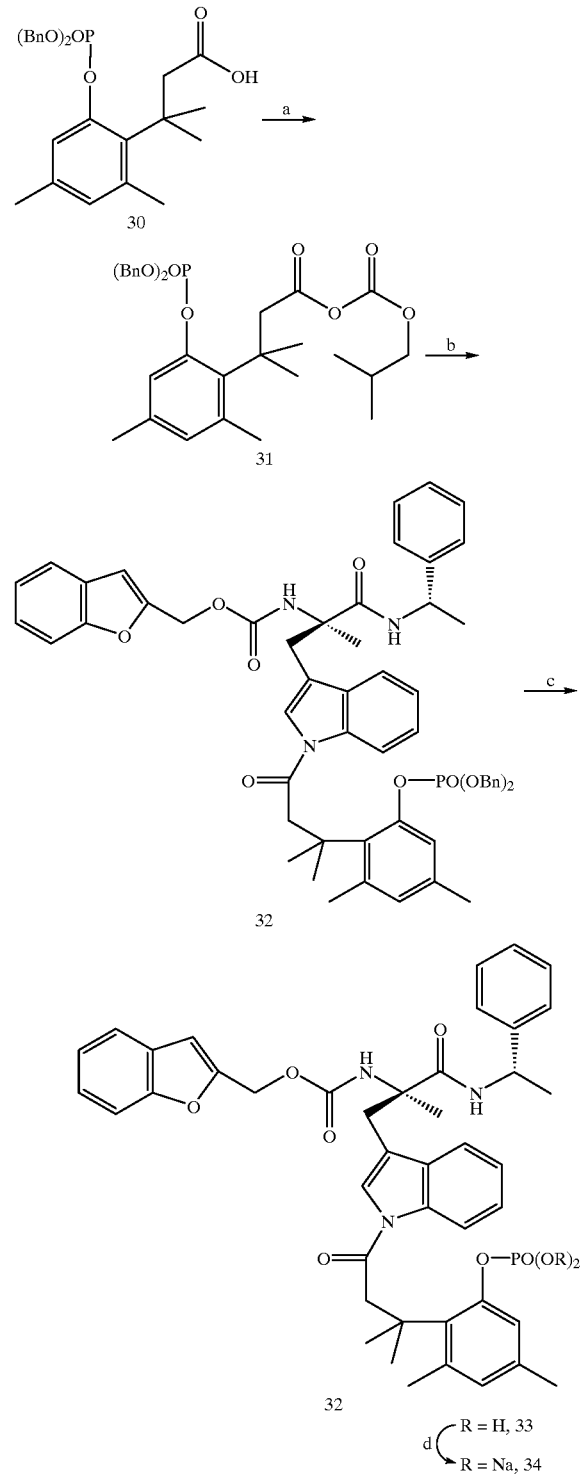

a. isobutyl chloroformate, NMM, CH₂Cl₂, -10° C.
b. KN(TMS)₂, THF -78° C., compound 1.
c. 1,4-cyclohexandiene 10% Pd/C, EtOH. d. 0.1M NaOH, H₂O.

[2-{1-[3-(2,4-Dimethyl-6-phosphonooxy-phenyl)-3-methylbutyryl]-1H-indol-3-yl}-1-methyl-1-(1-phenylethylcarbamoyl)ethyl]carbamic acid benzofuran-2-ylmethyl ester disodium salt (34)

Isobutyl chloroformate (1.846 mL, 14.23 mmol, 1.1 eq.) was added to a solution of compound 30 (1.42 mL, 12.94 mmol) in dry $CH_2Cl_2$ at $-11°$ C. under $N_2$ and stirred at $-11°$ C. for 1 hour, then at $-5°$ C. for 30 minutes. The reaction mixture was then washed sequentially with 10% citric acid solution (cold), saturated $NaHCO_3$ (cold), water, saturated NaCl and dried over anhydrous $Na_2SO_4$. The solvent was evaporated to give compound 31 as a brown oil. This mixed anhydride was used directly in the next reaction.

A solution of $KN(TMS)_2$ in toluene (0.5 M, 22.63 mL, 11.31 mmol, 1.05 eq.) was added dropwise to a solution of compound 1 (5.34 g, 10.78 mmol) in dry THF at $-78°$ C. under $N_2$ in about 10 minutes. The solution was then stirred at $-78°$ C. for 20 minutes. A solution of compound 31 (about 12.94 mmol) in dry THF (15 mL) was then added in one portion, and the reaction was stirred at $-78°$ C. for 30 minutes. The reaction mixture was diluted with EtOAc (1500 mL) and washed sequentially with saturated $NaHCO_3$ (2×500 mL), water (300 mL), saturated NaCl and dried over anhydrous $Na_2SO_4$. The solvent was evaporated to give a brown oil which was purified by silica gel chromatography (5.5×26 cm) eluting with $CHCl_3$/MeOH (10:0.02) to give compound 32 as a white foam (8.97 g, 87%).

$^1$H NMR ($CDCl_3$) δ 8.322 (d, J=7.1 Hz, 1H), 7.51–7.02 (m, 21H), 6.923 (d, J=7.1 Hz, 2H), 6.784 (s, 1H), 6.684 (s, 1H), 6.654 (s, 1H), 6.442 (bm, 2H), 5.118 (m, 2H), 4.955 (p, J=6.8 Hz, 1H), 4.796 (p, J=9.3 Hz, 2H), 4.642 (m, 2H), 3.498 (d, J=16.6 Hz, 1H), 3.396 (d, J=14.6 Hz, 1H), 3.149 (m, 2H), 2.484 (s, 3H), 2.055 (s, 3H), 1.562 (s, 3H), 1.443 (s, 6H), 1.313 (d, J=6.8 Hz, 3H).

MS (Scan AP+) m/z 960.6 (M+1, 10.8%).

Anal. Calcd for $C_{57}H_{58}N_3O_9P_1.H_2O$: C, 69.93; H, 6.13; N, 4.29. Found: C, 69.69; H, 6.00; N, 4.20.

1,4-Cyclohexandiene (1.12 mL, 11.8 mmol, 15 eq.) was added to a solution of compound 32 (2.14 g, 2.23 mmol) in ethanol (56 mL) with 10% Pd/C (0.214 g, 10%) under nitrogen at room temperature, and the reaction mixture was stirred at room temperature for 9 hours. The catalyst was removed by filtration through celite, and the solid cake was washed with ethanol. The combined filtrate was evaporated under reduced pressure to give a colorless foam (1.715 g, with 83% purity by HPLC). The foam was purified by preparative reverse phase HPLC (VYDAC, C18, 78×250 mm, 10–15μ) eluting with $CH_3CN$/0.1% TFA in $H_2O$ (10:1) to give, after evaporation of solvent and lyophilization, compound 33 as a white solid (1.11 g, 52%) with >99.5% purity by HPLC.

M.P.=turn soft>140° C.

$^1$H NMR ($CD_3OD$+1 drop of DCl) δ 8.167 (d, J=8.3 Hz, 1H), 7.53–6.98 (m, 15H), 6.785 (bs, 1H), 6.670 (s, 1H), 5.221 (q, 4H), 4.908 (q, 1H), 3.455 (m, 3H), 3.200 (d, J=14.4 Hz, 1H), 2.382 (s, 3H), 2.105 (s, 3H), 1.577 (s, 6H), 1.314 (d, J=6.8 Hz, 3H).

MS (Scan ES−) m/z 778.6 (M−1, 100%).

$[α]_D^{23}$=+43.2 (c 0.88, MeOH).

Anal. Calcd for $C_{43}H_{46}N_3O_9P_1.2.2H_2O$: C, 62.97; H, 6.15; N, 5.13. Found: C, 62.70; H, 5.76; N, 5.07.

A solution of NaOH (0.0995 M, 27.9 mL, 2.78 mmol) was added dropwise with stirring to a suspension of compound 33 (1.11 g, 1.39 mmol) in water (35 mL) to give a clear solution (final pH=8.8). The solution was lyophilized to give the disodium salt 34 as a white solid (1.12 g, 96%).

M.P.=turn soft>154° C.

$^1$H NMR ($CD_3OD$) δ 8.212 (d, J=8.2 Hz, 1H), 7.57–7.02 (m, 14H), 6.817 (s, 1H), 6.705 (s, 1H), 5.204 (m, 2H), 4.952 (q, 1H), 3.500 (m, 3H), 3.241 (d, J=14.2 Hz, 1H), 2.524 (s, 3H), 2.184 (s, 3H), 1.622 (s, 6H), 1.453 (s, 3H), 1.353 (d, J=7 Hz, 3H).

$^{31}$P NMR ($CD_3OD$, with external $H_3PO_4$/$CDCl_3$) δ −5.897.

MS (Scan ES−) m/z 778.6 (M−1, 100%).

$[α]_D^{23}$=31.5 (c 0.85, MeOH).

Anal. Calcd for $C_{43}H_{44}N_3O_9P_1Na_2.4H_2O$: C, 57.60; H, 5.80; N, 4.69; Na, 5.13. Found: C, 57.27; H, 5.38; N, 4.50; Na, 5.19.

What is claimed is:

1. A compound of Formula

I

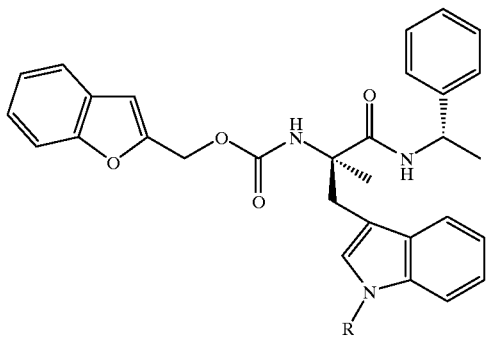

or a pharmaceutically acceptable salt thereof wherein

R is
—$CH_2OZ$;
—$C(=O)OCH_2OZ$ or Z;

wherein Z is

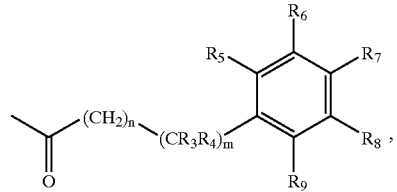

—$P(=O)(OH)_2$, or
—$C(=O)Q$;

n is an integer of from 0 to 3;

m is an integer of from 0 to 1;

$R_3$ and $R_4$ are each independently hydrogen or alkyl of from 1 to 6 carbons or $R_3$ and $R_4$ are taken together with the carbon to which they are attached to form a cycloalkylidene of from 3 to 6 carbons;

$R_5$–$R_9$ are each independently hydrogen, halogen, alkyl, or alkoxy and one of $R_5$–$R_9$ is —$OC(=O)Q$, $OP(=O)(OH)_2$, —$CH_2OC(C=O)Q$, —$CH_2OP(=O)(OH)_2$, —OH, $CH_2NR_1R_2$, or $NR_1R_2$;

Q is alkyl optionally substituted by —OH, phosphono, phosphooxy, carboxy, or amino, monoalkylamino, or dialkylamino;

$R_1$ and $R_2$ are each independently hydrogen, alkyl optionally substituted with —OH, phosphono, phosphonooxy, carboxy, or dialkyl amino or $NR_1R_2$ is

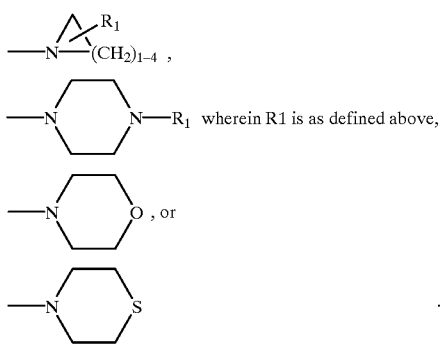

wherein R1 is as defined above,

2. A compound according to claim 1 wherein R is $CH_2OZ$.
3. A compound according to claim 1 wherein R is $-C(=O)OCH_2OZ$.
4. A compound according to claim 1 wherein R is $-CH_2OZ$ or $-C(=O)OCH_2OZ$ wherein Z is

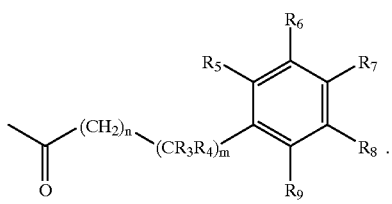

5. A compound according to claim 1 wherein R is $-CH_2OZ$ or $-C(=O)OCH_2OZ$ wherein Z is $-P(=O)(OH)_2$.
6. A compound according to claim 1 wherein R is $-CH_2OZ$ or $-C(=O)OCH_2OZ$ wherein Z is $-C(=O)Q$.
7. A compound according to claim 1 and selected from:

[2-(1-Hydroxymethyl-1H-indol-3-yl)-1-methyl-1-(1-phenyl-ethylcarbamoyl)-ethyl]-carbamic acid benzofuran-2-ylmethyl ester;

3-[2-(Benzofuran-2-ylmethoxycarbonylamino)-2-(1-phenyl-ethylcarbamoyl)-propyl]-indole-1-carboxylic acid 4-phosphonooxymethyl-benzoyloxymethyl ester;

3-[2-(Benzofuran-2-ylmethoxycarbonylamino)-2-(1-phenyl-ethylcarbamoyl)-propyl]-indole-1-carboxylic acid 4-dimethylamino-methyl-benzoyloxymethyl ester;

{1-Methyl-1-(1-phenyl-ethylcarbamoyl)-2-[1-(2-phosphonooxymethyl-benzoyl)-1H-indol-3-yl]-ethyl}-carbamic acid benzofuran-2-ylmethyl ester;

Dimethylamino-acetic acid 2-{3-[2-(benzofuran-2-ylmethoxycarbonylamino)-2-(1-phenyl-ethylcarbamoyl)-propyl]-indole-1-carbonyl}-benzyl ester;

[2-{1-[3-(2,4-Dimethyl-6-phosphonooxy-phenyl)-3-methylbutyryl]-1H-indol-3-yl}-1-methyl-1-(1-phenyl-ethylcarbamoyl)-ethyl]-carbamic acid benzofuran-2-ylmethyl ester;

{3-[2-Benzofuran-2-ylmethoxycarbonylamino)-2-(1-phenyl-ethylcarbamoyl)-propyl]-indol-1-yl}-phosphonic acid;

3-[2-(Benzofuran-2-ylmethoxycarbonylamino-2-(1-phenyl-ethylcarbamoyl)-propyl]-indole-1-carboxylic acid 4-morpholin-4-ylmethyl-benzoyloxymethyl ester;

3-[2-(Benzofuran-2-ylmethoxycarbonylamino)-2-(1-phenyl-ethylcarbamoyl)-propyl]-indole-1-carboxylic acid 4-(4-methyl-piperazin-1-ylmethyl)-benzoyloxymethyl ester;

3-[2-(Benzofuran-2-ylmethoxycarbonylamino)-2-(1-phenyl-ethylcarbamoyl)-propyl]-indole-1-carboxylic acid 4-[4-(2-hydroxy-ethyl)-piperazin-1-ylmethyl]-benzoyloxymethyl;

3-[2-(Benzofuran-2-ylmethoxycarbonylamino)-2-(1-phenyl-ethylcarbamoyl)-propyl]-indole-1-carboxylic acid 4-{[(2-dimethylamino-ethyl)-methyl-amino]-methyl}-benzoyloxymethyl ester;

3-[2-(Benzofuran-2-ylmethoxycarbonylamino)-2-(1-phenyl-ethylcarbamoyl)-propyl]-indole-1-carboxylic acid 4-{[bis-(2-hydroxyethyl)-amino]-methyl}-benzoyloxymethyl ester;

3-[2-(Benzofuran-2-ylmethoxycarbonylamino)-2-(1-phenyl-ethylcarbamoyl)-propyl]-indole-1-carboxylic acid 4-(3-hydroxy-pyrrolidin-1-ylmethyl)-benzoyloxymethyl ester;

3-[2-(Benzofuran-2-ylmethoxycarbonylamino)-2-(1-phenyl-ethylcarbamoyl)-propyl]-indole-1-carboxylic acid 4-piperazin-1-ylmethyl-benzoyloxymethyl ester; and 1,4-Piperazinediylbis[methylene-4,1-phenylenecarboxymethylene][R-(R*,S*)]-3-[2-[[2-benzofuranylmethoxy)carbonyl]amino]-2-methyl-3-oxo-3-[(1-phenylethyl)amino]propyl]-1H-indole-1-carboxylate or a pharmaceutically acceptable salt thereof.

8. A pharmaceutical composition comprising a therapeutically effective amount of a compound of claim 1 in unit dosage form, and a pharmaceutically acceptable carrier.

9. A method for treating emesis in a mammal which comprises administering to a mammal in need thereof an effective amount of a compound of claim 1.

10. A method for treating respiratory disorders in a mammal which comprises administering to a mammal in need thereof an effective amount of a compound of claim 1.

11. A method for treating asthma in a mammal which comprises administering to a mammal in need thereof an effective amount of a compound of claim 1.

12. A method for treating inflammation in a mammal which comprises administering to a mammal in need thereof an effective amount of a compound of claim 1.

13. A method for treating arthritis in a mammal which comprises administering to a mammal in need thereof an effective amount of a compound of claim 1.

14. A method for treating gastrointestinal disorders in a mammal which comprises administering to a mammal in need thereof an effective amount of a compound of claim 1.

15. A method for treating ophthalmic disease in a mammal which comprises administering to a mammal in need thereof an effective amount of a compound of claim 1.

16. A method for treating allergies in a mammal which comprises administering to a mammal in need thereof an effective amount of a compound of claim 1.

17. A method for treating migraine in a mammal which comprises administering to a mammal in need thereof an effective amount of a compound of claim 1.

18. A method for treating inflammatory pain or neurogenic pain in a mammal which comprises administering to a mammal in need thereof an effective amount of a compound of claim 1.

19. A method for treating atherosclerosis in a mammal which comprises administering to a mammal in need thereof an effective amount of a compound of claim 1.

20. A method for treating rheumatoid arthritis in a mammal which comprises administering to a mammal in need thereof an effective amount of a compound of claim 1.

* * * * *